United States Patent
Serena et al.

(10) Patent No.: US 7,392,140 B2
(45) Date of Patent: Jun. 24, 2008

(54) CELLULAR FIBRONECTIN AS A DIAGNOSTIC MARKER IN STROKE AND METHODS OF USE THEREOF

(75) Inventors: Joaquín Serena, Girona (ES); Antoni Dãvalos, Girona (ES); Mar Castellanos, Girona (ES); José Castillo, Santiago de Compostela (ES); Cornelius Allen Diamond, San Diego, CA (US)

(73) Assignee: Prediction Sciences, LLC, La Jolla, CA (US)

( * ) Notice: Subject to any disclaimer, the term of this patent is extended or adjusted under 35 U.S.C. 154(b) by 0 days.

(21) Appl. No.: 11/346,862

(22) Filed: Feb. 1, 2006

(65) Prior Publication Data

US 2007/0005261 A1 Jan. 4, 2007

Related U.S. Application Data

(63) Continuation-in-part of application No. 11/046,592, filed on Jan. 29, 2005, now abandoned, which is a continuation-in-part of application No. 10/948,834, filed on Sep. 22, 2004.

(60) Provisional application No. 60/505,606, filed on Sep. 23, 2003, provisional application No. 60/556,411, filed on Mar. 24, 2004.

(51) Int. Cl.
 *A61B 5/00* (2006.01)
 *G01N 33/48* (2006.01)
 *G01N 33/50* (2006.01)
 *G06F 19/00* (2006.01)

(52) U.S. Cl. ............ 702/19; 435/7.1; 436/510; 600/300; 600/301

(58) Field of Classification Search ............ 702/19; 435/7.1; 436/510; 600/300, 301
See application file for complete search history.

(56) References Cited

U.S. PATENT DOCUMENTS 5,079,171 A * 1/1992 Senyei et al. ............... 436/510
2003/0100010 A1 * 5/2003 Jackowski et al. ........... 435/7.1

OTHER PUBLICATIONS

Hegele et al. Database Caplus, DN: 141:377907, 2004.*

* cited by examiner

*Primary Examiner*—Michael Borin
(74) *Attorney, Agent, or Firm*—Fuess & Davidenas

(57) ABSTRACT

Methods for the diagnosis and evaluation of stroke and stroke sub-type employ a variety of bio-markers including cellular fibronectin (c-Fn) assembled as a panel for stoke diagnosis and evaluation. Methods are disclosed for selecting markers and correlating their combined levels with a clinical outcome of interest. In various aspects the methods permit early detection and differentiation of stroke subtypes, determination of the prognosis of a patient presenting stroke symptoms, and identification of a patient at risk for early hematoma growth and/or malignant massive cerebral artery infarction. The disclosed methods provide rapid, sensitive and specific assays to greatly increase the number of patients that can receive beneficial stroke treatment and therapy, and to reduce the human and economic costs associated with incorrect stroke diagnosis.

19 Claims, 6 Drawing Sheets

FIGURE 1

|  | Non-EHG (n=129) | EHG (n=54) |
|---|---|---|
| Age, y | 71 (10) | 69 (9.8) |
| Sex, male | 55% | 63% |
| Time to inclusion | 5.9 (2.8) | 5.7 (3.0) |
| Epidemiological characteristics |  |  |
| History of hypertension | 65% | 61% |
| Alcohol abuse (>40g/d) | 23.3% | 18.6% |
| Smoking (>10 cigarettes/d) | 13.3% | 16.7% |
| Previous diabetes | 19.4% | 13% |
| Previous hepatopathy | 10% | 13% |
| Previous TIA/stroke | 14.7% | 5.6% |
| Previous cognitive decline | 6.2% | 9.3% |
| Previous infection (within 15 days) | 5.4% | 11% |
| Clinical characteristics |  |  |
| Seizures at onset | 11.6% | 5.6% |
| Headache at onset | 27% | 31.5% |
| Canadian Scale Score | 5 [3, 6.5] | 4 [2.5, 6.5] |
| Body temperature, °C | 36.5 (0.5) | 36.7 (0.7) |
| Systolic blood pressure, mm Hg | 176 (25) | 178 (34) |
| Diastolic blood pressure, mm Hg | 99 (18) | 94.7 (19) |
| Biochemical parameters |  |  |
| Serum glucose, mg/dL | 144 (47) | 151 (46) |
| Leucocyte count, ×1000/mmc | 9.4 (6.0) | 10.3 (3.8)* |
| Platelet count, ×1000/mmc | 204 (54) | 185 (66)* |
| Fibrinogen, mg/dL | 408 (116) | 452 (119)* |
| Prothrombin time, % | 93 (9) | 95 (7) |
| aPTT, seconds | 28.5 (3.0) | 28.9 (4.0) |
| Neuroimaging findings |  |  |
| ICH volume, mL | 26.5 [12.5; 47] | 25 [16; 61] |
| Volume of peripheral hypodensity, mL | 5.0 [2.0;13] | 8.3 [2.5; 26]* |
| Intraventricular bleeding | 35.7% | 18.5%* |
| Peripheral hypodensity | 89% | 90.7% |
| Leukoaraiosis | 43.4% | 37% |
| Lobar location | 28% | 20.4% |
| Mass effect | 52% | 64% |

Continuous data are expressed as mean (SD) or median [quartiles].
*$P<0.05$.
EHG indicates early hematoma growth; aPTT, activated partial thromboplastin time; TIA, transient ischemic attack.

FIGURE 2

|  | Non-EHG (n=129) | EHG (n=54) |
|---|---|---|
| IL-6, pg/mL | 15.9 [11.5; 19.8] | 19.6 [13.6; 29.9] |
| TNF-$\alpha$, pg/mL | 8.7 [4.7; 13.5] | 13.5 [8.4; 30.5] |
| MMP-9, ng/mL | 70.6 [47.8; 103.8] | 153.3 [117.7; 204.7] |
| C-Fn, $\mu$g/mL | 2.8 [1.6; 4.2] | 8.8 [6.2; 12.5] |

Numbers in square brackets are quartiles.
All comparisons, $P<0.001$.

FIGURE 3

|  | OR | 95% CI | P |
|---|---|---|---|
| Volume of peripheral hypodensity, mL | 1.02 | 0.99–1.05 | 0.20 |
| Intraventricular bleeding | 0.24 | 0.06–0.90 | 0.03 |
| Leukocytes >11×1000/mmc | 0.87 | 0.17–4.4 | 0.87 |
| Platelets ×1000/mmc | 0.99 | 0.98–1.00 | 0.30 |
| Fibrinogen, mg/dL | 1.00 | 0.99–1.01 | 0.08 |
| IL-6 >24 pg/mL | 16 | 2.3–119 | 0.005 |
| TNF-$\alpha$ >20 pg/mL | 0.55 | 0.07–4.3 | 0.57 |
| MMP-9 >140 ng/mL | 1.69 | 0.49–5.8 | 0.40 |
| c-FN >6 $\mu$g/mL | 92 | 22–381 | <0.001 |

FIGURE 4

|  | m-MCA Infarction (n=40) | Non-mMCA Infarction (n=35) | p |
|---|---|---|---|
| Sex, male, n (%) | 28 (70) | 21 (60) | 0.47 |
| Age, y | 59.7 (7.2) | 65.0 (6.5) | <0.01 |
| Patients >60 y of age, n (%) | 19 (47.5) | 30 (85.7) | <0.001 |
| Mean time from stroke onset to blood sampling, hours | 5.3 (2.6, 9) | 6.5 (2.5, 9) | 0.63 |
| Previous infectious disease or hyperthermia, n (%) | 4 (10.0) | 4 (11.4) | 1.0 |
| Clinical characteristics | | | |
| CSS on admission | 3.5 (3.5) | 3.5 (2.5,5) | 0.75 |
| Suspected etiology | | | 0.81 |
| Large-artery atherosclerosis | 35.0% | 42.9% | |
| Cardioembolism | 55.0% | 45.7% | |
| Cryptogenic stroke | 10.0% | 11.4% | |
| Biochemistry and vital signs at admission | | | |
| Plasma glucose, mg/dL | 144.5 (49.0) | 155.5 (48.0) | 0.34 |
| Plasma fibrinogen, mg/dL | 546.0 (206.2) | 485.5 (154.7) | 0.17 |
| Leukocyte count, no.×$10^3$/mm$^3$ | 9.9 (2.7) | 9.0 (2.4) | 0.12 |
| Erythrocyte sedimentation rate, mm/hour | 24.6 (22.4) | 25.3 (16.4) | 0.90 |
| Systolic blood pressure, mm Hg | 149.4 (20.1) | 147.7 (26.4) | 0.13 |
| Diastolic blood pressure, mm Hg | 85.1 (14.3) | 80.0 (14.9) | 0.17 |
| Body temperature, °C | 36.6 (0.7) | 36.9 (0.7) | 0.07 |
| Outcome | | | |
| Early neurological deterioration | 100% | 25.7% | <0.001 |
| Mortality | 67.5% | 20.0% | <0.001 |
| CSS at 3 months | 1.5 (1.5, 3.8) | 5.5 (4.7) | <0.001 |
| Modified Rankin scale >2 at 3 months | 97.5% | 77.1% | 0.01 |

Continuous variables are expressed as mean (SD) or median values and quartiles as appropriate.

FIGURE 5

|  | At Baseline | | |
|---|---|---|---|
|  | m-MCA Infarction (n=40) | non-mMCA Infarction (n=35) | P |
| Glutamate, μmol/L | 147.2 (88–239.9) | 84.6 (57.2–188.6) | 0.02 |
| Glycine, μmol/L | 203 (98) | 192 (77) | 0.58 |
| GABA, nmol/L | 286 (131) | 315 (144) | 0.38 |
| IL-6, pg/mL | 18.9 (10.8) | 18.2 (12.6) | 0.82 |
| IL-10, pg/mL | 6.7 (2.1) | 6.6 (2.3) | 0.84 |
| TNF-α, pg/mL | 18.1 (6.8) | 19.0 (6.6) | 0.62 |
| MMP-9, ng/mL | 150 (66) | 78 (59) | <0.001 |
| c-Fn, μg/mL | 25.3 (33.7, 50.2) | 4.2 (6.7, 10.9) | <0.001 |

Values are expressed as mean (SD) or median values and quartiles as appropriate.

FIGURE 6

|  | Sensitivity (%) | Specificity (%) | PPV (%) | NPV (%) |
|---|---|---|---|---|
| Age >50 vs ≤50 y | 12.5 | 97.1 | 83.3 | 49.3 |
| Age >60 vs ≤60 y | 52.5 | 85.7 | 80.8 | 61.2 |
| Early signs of brain infarction | 93 | 75 | 93 | 26 |
| Hypodensity | 63 | 40 | 63 | 29 |
| ASPECTS ≤7 | 56 | 31 | 56 | 55 |
| ASPECTS ≤4 | 81 | 89 | 81 | 57 |
| MMP (≥140 ng/mL) | 64 | 88 | 85 | 69 |
| c-Fn (≥16.6 μg/mL) | 90 | 100 | 100 | 90 |

CELLULAR FIBRONECTIN AS A DIAGNOSTIC MARKER IN STROKE AND METHODS OF USE THEREOF

REFERENCE TO RELATED APPLICATIONS

The present application is a continuation-in-part of U.S. utility patent application Ser. No. 11/046,592 filed Jan. 29, 2005 now abandoned, which is a continuation-in-part of U.S. utility patent application Ser. No. 10/948,834 filed Sep. 22, 2004, which application is itself descended from U.S. provisional patent applications 60/505,606 filed Sep. 23, 2003 and 60/556,411 filed Mar. 24, 2004, the contents of all of which are hereby incorporated herein in their entirety, including all tables, figures, and claims.

BACKGROUND OF THE INVENTION

1. Field of the Invention

The present invention generally relates to the identification and use of diagnostic markers for cerebral injury. In a various aspects, the present invention particularly relates to methods for (1) the early detection and differentiation of secondary brain edema; (2) early growth of intracerebral hemorrhage (ICH); and (3) to identify patients who could benefit from aggressive therapies such as decompressive hemicraniectomy or hypothermia.

2. Background of the Invention

The following discussion of the background of the invention is merely provided to aid the reader in understanding the invention and is not admitted to describe or constitute prior art to the present invention.

A stroke is a sudden interruption in the blood supply of the brain. Most strokes are caused by an abrupt blockage of arteries leading to the brain (ischemic stroke). Other strokes are caused by bleeding into brain tissue when a blood vessel bursts (hemorrhagic stroke). Because stroke occurs rapidly and requires immediate treatment, stroke is also called a brain attack. When the symptoms of a stroke last only a short time (less than an hour), this is called a transient ischemic attack (TIA) or mini-stroke. Stroke has many consequences.

The effects of a stroke depend on which part of the brain is injured, and how severely it is injured. A stroke may cause sudden weakness, loss of sensation, or difficulty with speaking, seeing, or walking. Since different parts of the brain control different areas and functions, it is usually the area immediately surrounding the stroke that is affected. Sometimes people with stroke have a headache, but stroke can also be completely painless. It is very important to recognize the warning signs of stroke and to get immediate medical attention if they occur.

Stroke or brain attack is a sudden problem affecting the blood vessels of the brain. There are several types of stroke, and each type has different causes. The three main types of stroke are listed below.

Ischemic stroke is the most common-type of stroke—accounting for almost 80% of strokes—and is caused by a clot or other blockage within an artery leading to the brain.

Intracerebral hemorrhage (ICH) is a type stroke caused by the sudden rupture of an artery within the brain. Blood is then released into the brain, compressing brain structures.

Subarachnoid hemorrhage is also a type of stroke caused by the sudden rupture of an artery. A subarachnoid hemorrhage differs from an intracerebral hemorrhage in that the location of the rupture leads to blood filling the space surrounding the brain rather than inside of it.

ICH causes a 35% to 50% 30-day mortality. Half of this mortality occurs within the first 2 days as a result of brain herniation, mainly caused by the continued bleeding that provokes an enlargement of the hematoma during the first 24 hours (Kazui S, Naritomi H, Yamamoto H, Sawada T, Yamaguchi T. Enlargement of spontaneous intracerebral hemorrhage. Incidence and time course. *Stroke*. 1996; 27:1783-1787.). Early hematoma growth (EHG) has been associated with early neurological worsening and poor outcome, but no clinical or radiological predictive factors have been identified and the pathogenesis remains unclear (see for instance Brott T, Broderick J, Kothari R, Barsan W, Tomsick T, Sauerbeck L, Spilker J, Duldner J, Khouri J. Early hemorrhage growth in patients with intracerebral hemorrhage. *Stroke*. 1997; 28:1-5; Fujii Y, Tanaka R, Takeuchi S, Koike T, Minakawa T, Sasaki O. Hematoma enlargement in spontaneous intracerebral hemorrhage. *J Neurosyrg*. 1994; 80:51-57.).

The pathophysiology of brain edema and secondary neuronal injury in ICH is as follows. After the initial arterial rupture, the activation of the coagulation cascade produces a large quantity of thrombin that is implicated in several functions, including chemotaxis of leukocytes, expression of adhesion molecules, release of inflammatory cytokines, blood-brain barrier disruption, and local metalloproteinase generation (see for instance Xi G et al 1998; Lee K R, Colon G P, Betz A L, Keep R F, Kim S, Hoff J T. Edema from intracerebral hemorrhage: the role of thrombin. *J. Neurosurg*. 1996; 84:91-96.). Furthermore, the release of iron after erythrocyte lysis may contribute to blood-brain barrier dysfunction, possibly through a free radical-mediated damage of endothelial wall (see for instance Xi G, Hua Y, Bhasin R R, Ennis S R, Keep R F, Hoff J T. Mechanisms of edema formation after intracerebral hemorrhage. Effects of extravasated red blood cells on blood flow and blood-brain barrier integrity. *Stroke*. 2001; 32:2932-2938.). Although all these mechanisms seem to be involved in edema formation after ICH (see for instance Castillo et al 2002; Abilleira S, Montaner J, Molina C, Monasterio J, Castillo J, Alvarez-Sabý'n J. Matrix metalloproteinase-9 concentration alter spontaneous intracerebral hemorrhage. *J Neurosurg*. 2003; 99:65-70.), their role in the EHG remains unclear.

EHG has been related to multifocal bleeding in the periphery of the clot caused by the rupture of arterioles and venules in the perilesional low-flow zone. Secondary brain injury has been attributed to ischemic damage and particularly to the toxic effects of thrombin generation by the clot (see for example Mendelow A D. Mechanisms of ischemic brain damage with intracerebral hemorrgae. *Stroke*. 1993; 24(suppl 1):115-117.). In experimental ICH, thrombin activates the inflammatory cascade and the expression of matrix metalloproteinases (MMPs), causing the breakdown of the blood-brain barrier and edema formation (see for example Xi G, Wagner K R, Keep R F, Hua Y, de Courten-Mayers G, Broderick J P, Brott T G, Hoff J T. Role of blood clot formation on early edema development after experimental intracerebral hemorrhage. *Stroke*. 1998; 29:2580-2586; Rosenberg G A, Navratil M. Metalloproteinase inhibition blocks edema in intracerebral hemorrhage in the rat. *Neurology*. 1997; 48: 921-926.). In this context, high serum concentrations of cytokines and MMP-9 have been associated with a large volume of peripheral hypodensity in human ICH (see for example Castillo J, Davalos A, Alvarez-Sabin J, Pumar J M, Leira R, Silva Y, Montaner J, Kase C S. Molecular signatures of brain injury after intracerebral hemorrhage. *Neurology*. 2002; 58:624-629.). MMPs are able to degrade the basal membrane components, such as cellular fibronectin (c-Fn), a glycoprotein especially important for the adhesion of platelets to fibrin, a function necessary for the blockade of bleeding.

The knowledge of the underlying mechanisms and factors associated with EHG is crucial because they represent potential targets for therapeutic interventions. In the only previous prospective study, Brott et al. failed to reveal any clinical, radiological, or analytic predictor of ICH growth (Brott T, Broderick J, Kothari R, Barsan W, Tomsick T, Sauerbeck L, Spilker J, Duldner J, Khouri J. Early hemorrhage growth in patients with intracerebral hemorrhage. *Stroke*. 1997; 28: 1-5.).

Massive middle cerebral artery (MCA) infarction accounts for 10% to 15% of all MCA infarctions, and of these patients, malignant MCA (m-MCA) reaches 40% to 50%. The syndrome of m-MCA infarction, which is attributable to brain edema, is more frequent in younger patients and has a poor prognosis both short and long term. In 80% of patients, it leads to death, and those patients who survive experience severe neurological deficits.

Conservative treatments fail to improve mortality and disability. Early hemicraniectomy and hypothermia are feasible and have been proposed as effective treatments for this condition because they change the natural history of the disease.5 However, those patients who will develop m-MCA syndrome are currently not revealed by clinical, neuroimaging, or biochemical markers sufficiently early and with sufficient accuracy as to indicate an aggressive management.

The loss of integrity of the endothelial basal lamina is believed to be the primary cause of edema after focal cerebral ischemia. Matrix metalloproteinase-9 (MMP-9), a proteolytic zinc-dependent enzyme for which expression is increased during stroke (for example see Clark A W, Krekoski C A, Bou S S, Chapman K R, Edwards D R. Increased gelatinase A (MMP-2) and gelatinase B (MMP-9) activities in human brain after focal ischemia. *Neurosci Lett*. 1997; 238: 53-56.), and in experimental models of focal ischemia, 9 it degrades the endothelial basal lamina10 and plays an essential role in producing edema and hemorrhagic transformation (for example see Hoe Heo J, Lucero J, Abumiya T, Koziol J A, Copeland B R, del Zoppo G J. Matrix metalloproteinases increase very early during experimental focal cerebral ischemia. *J Cereb Blood Flow Metab*. 1999; 19:624-633; Rosenberg G A, Mun-Bryce S, Wesley M, Kornfeld M. Collagenase induced intracerebral hemorrhage in rats. *Stroke*. 1990; 21:801-807.).

In a recent study, serum cellular-fibronectin (c-Fn), a component of the basal lamina, was shown to be a more accurate predictor of hemorrhagic transformation than MMP-9 in acute ischemic stroke patients treated with tissue plasminogen activator (tPA). (For example see Castellanos M, Leira R, Serena J, Blanco M, Pedraza S, Castillo J, Davalos A. Plasma cellular-fibronectin concentration predicts hemorrhagic transformation after thrombolytic therapy in acute ischemic stroke. *Stroke*. 2004; 35:1671-1676.) Therefore, an increased expression of blood-brain barrier (BBB) disruption markers in cerebral ischemia may partially explain the syndrome of m-MCA infarction. The instant invention shows the association between plasma concentrations of MMP-9, c-Fn, excitatory amino acids (EAAs), and inflammatory molecules with the development of brain edema and subsequent m-MCA syndrome in patients with complete MCA infarction.

Results for mortality rate and functional outcome after hemicraniectomy in massive MCA infarction have been contradictory (for example see Schwab S, Steiner T, Aschoff A, Schwarz S, Steiner H H, Jansen O, Hacke W. Early hemicraniectomy in patients with complete middle cerebral artery infarction. *Stroke*. 1998; 29:1888-1893; Morley N C D, Berge E, Cruz-Flores S, Whittle I R. Surgical decompression for cerebral oedema in acute ischaemic stroke (Cochrane Review). In the Cochrane Library. 2003, Issue 3. Oxford, UK: Update Software; 2003.). This might be explained by the lack of reliable predictors of m-MCA infarction. Studies into the value of neuroimaging and clinical and biochemical markers of malignant brain edema have found few predictors to be sufficiently sensitive and specific as to be useful in clinical practice (Table 5). Clinical factors alone are not sufficient to identify patients with impending brain edema (for example see Kasner S E, Demchuk A M, Berrouschot J, Schmutzhard E, Harms L, Verro P, Chalela J A, Abbur R, McGrade H, Christou I, Krieger D W. Predictors of fatal brain edema in massive hemispheric ischemic stroke. *Stroke*. 2001; 32:2117-2123; Krieger D W, Demchuk A M, Kasner S E, Jauss M, Hantson L. Early clinical and radiological predictors of fatal brain swelling in ischemic stroke. *Stroke*. 1999; 30:287-292.). CT scan showed acceptable sensitivity in some studies but low specificity in identifying candidates for hemicraniectomy (for example see von Kummer R, Meyding-Lamade U, Forsting M, Rosin L, Rieke K, Hacke W, Sartor K Sensitivity and prognostic value of early CT in occlusion of the middle cerebral artery trunk. *AJNR Am J Neuroradiol*. 1994; 15:9-15; Berrouschot J, Sterker M, Bettin S, Koster J, Schneider D. Mortality of space-occupying ("malignant") middle cerebral artery infarction under conservative intensive care. *Intensive Care Med*. 1998; 24:620-623.). A recent approach has been to monitor biochemical markers and intracranial pressure (ICP) using a microdialysis probe inserted into the brain tissue (for example see Dohmen C, Bosche B, Graf R, Staub F, Kracht L, Sobesky J, Neveling M, Brinker G, Heiss W-D. Prediction of malignant course in MCA infarction by PET and microdialysis. *Stroke*. 2003;34:2152-2158.). However, this technique is complex, not widely available, invasive, and did not predict fatal outcome early enough for the successful implementation of invasive therapies because clinical deterioration often preceded the appearance of the analyzed biochemical markers and increased ICP. Promising results have been obtained with recent neuroimaging tests such as single-photon emission CT (for example see Berrouschot J et al. 1998), positron emission tomography of C-flumazenil (for example see Dohmen C et al. 2003), and diffusion-weighted MRI (for example see Oppenheim C, Samson Y, Manai R, Lalam T, Vandamme X, Crozier S, Srour A, Cornu P, Dormont D, Rancurel G, Marsault C. Prediction of malignant middle cerebral artery infarction by diffusion-weighted imaging. *Stroke*. 2000; 31:2175-2181. Thomalla G J, Kucinski T, Schoder V, Fiehler J, Knab R, Zeumer H, Weiller C, Rother J. Prediction of malignant middle cerebral artery infarction by early perfusion and diffusion-weighted magnetic resonance imaging. *Stroke*. 2003; 34:1892-1899.) in the prediction of m-MCA infarction within the suggested time window for hemicraniectomy. However these techniques evaluate infarct volume, the most reliable predictor of m-MCA, quickly and accurately but are unable to predict the development of massive brain edema directly as well as being very expensive as compared to the instant invention.

Accordingly, there is a present need in the art for a rapid, sensitive and specific differential diagnostic assay for the early detection and differentiation of EHG, m-MCA, and to identify patients who could benefit from aggressive therapies such as decompressive hemicraniectomy or hypothermia. Such a diagnostic assay would greatly increase the number of patients that can receive beneficial stroke treatment and therapy and in so doing reduce the costs associated with incorrect stroke diagnosis. Some content of this patent application was first published in the journal Stroke in its May 5 and Aug. 11, 2005, electronic issues, and thus we claim priority from these dates as well as the aforementioned dates.

BRIEF SUMMARY OF THE INVENTION

The present invention relates to the identification and use of diagnostic markers for stroke, endothelial damage and detection of brain edema and ICH, and prediction of m-MCA and EHG following ICH. The methods and compositions described herein can meet a need in the healing arts for rapid, sensitive and specific diagnostic assay to be used in the diagnosis and differentiation of various neurological events. Moreover, the methods and compositions of the present invention can also be used to facilitate the treatment of stroke patients and the development of additional diagnostic and/or prognostic indicators.

In various aspects, the present invention relates to (1) materials and procedures for identifying markers that are associated with the diagnosis, prognosis, or differentiation of stroke and/or and prediction of m-MCA or EHG following ICH in a patient; (2) using such markers in diagnosing and treating a patient and/or monitoring the course of a treatment regimen; (3) using such markers to identify subjects at risk for one or more adverse outcomes related to stroke and/or may benefit from therapies such as hemicraniectomy; and (4) using at one of such markers an outcome marker for screening compounds and pharmaceutical compositions that might provide a benefit in treating or preventing such conditions.

In one of its aspects, the invention discloses methods for determining a diagnosis or prognosis related to a neurological event such as stroke, or for differentiating between stroke sub-type, and prediction of m-MCA or EHG following ICH, and/or predicting subsequent enlargement of the hematoma after ICH. The preferred method includes analyzing a fluid sample obtained from a person who has an unknown diagnosis for the levels of one or more markers specific to the damage caused by said neurological event. In the case of stroke, these markers would be drawn from the group consisting of markers relating to vascular damage, glial activation, inflammatory mediation, thrombosis, cellular injury, apoptosis, myelin breakdown, and specific and non-specific markers of cerebral injury. The analysis of the preferred method thus more precisely includes identifying one or more markers the presence or amount of which is associated with the diagnosis, prognosis, or differentiation of stroke, determination of m-MCA or ICH, and/or predicting prediction of m-MCA or EHG following ICH. Once such marker(s) are identified, the level of such marker(s) in a sample obtained from a subject of interest can be measured. In certain embodiments of the preferred method, these markers can be compared to a level that is associated with the diagnosis, prognosis, or differentiation of stroke including determination of m-MCA or ICH, and/or predicting subsequent m-MCA or EHG following ICH. By correlating the subject's marker level(s) to the diagnostic marker level(s), the presence or absence of stroke, and also the probability of future adverse outcomes, etc., in a patient may be rapidly and accurately determined.

In another of its aspects, the instant invention is embodied in methods for choosing one or more marker(s) for differentiation of stroke, including determination of m-MCA or ICH, and/or prediction of m-MCA or EHG following ICH that together, and as a group, have maximal sensitivity, specificity, and predictive power. Said maximal sensitivity, specificity, and predictive power is in particular realized by choosing one or more markers as constitute a group by process of plotting receiver operator characteristic (ROC) curves for (1) the sensitivity of a particular combination of markers versus (2) specificity for said combination at various cutoff threshold levels. In addition, the instant invention further discloses methods to interpolate the nonlinear correlative effects of one or more markers chosen by any methodology to such that the interaction between markers of said combination of one or more markers promotes maximal sensitivity, specificity, and predictive accuracy in the prediction of any of the occurrence of stroke, identification of stroke subtype, determination of m-MCA or ICH, and/or prediction of m-MCA or EHG following ICH.

For purposes of the following discussion, the methods described as applicable to the diagnosis and prognosis of stroke generally may be considered applicable to the diagnosis and prognosis of other ischemic events.

The term "marker" as used herein refers to proteins or polypeptides to be used as targets for screening test samples obtained from subjects. "Proteins or polypeptides" used as markers in the present invention are contemplated to include any fragments thereof, in particular, immunologically detectable fragments. One of skill in the art would recognize that proteins which are released by cells of the central nervous system which become damaged during a cerebral attack could become degraded or cleaved into such fragments. Additionally, certain markers are synthesized in an inactive form, which may be subsequently activated, e.g., by proteolysis. Examples of such markers are described hereinafter. The term "related marker" as used herein refers to one or more fragments of a particular marker that may be detected as a surrogate for the marker itself. These related markers may be, for example, "pre," "pro," or "prepro" forms of markers, or the "pre," "pro," or "prepro" fragment removed to form the mature marker. Exemplary markers that are synthesized as pre, pro, and prepro forms are described hereinafter. In preferred embodiments, these "pre," "pro," or "prepro" forms or the removed "pre," "pro," or "prepro" fragments are used in an equivalent fashion to the mature markers in the methods described herein.

Preferred markers of the invention can aid in the determination of m-MCA or ICH, and/or predicting subsequent enlargement of the hematoma after ICH. Preferred markers are drawn from the group including c-Fn, MMP-9, myelin basic protein, IL-1, IL-1α, IL-1β, IL-6, IL-8, IL-10, NCAM, VCAM, ICAM, S100β, GFAP, BNGF, CRP, β-TG, PF-4, D-Dimer, TGF-α, NT-3, $F_{1+2}$, VEGF, CK-BB, caspase 3, MCP-1, thrombin-antithrombin III complex, tissue factor, GFAP, NSE-γγ, vWF, VEGF, FPA, and NR2A/2B. Each of these terms are defined hereinafter. Particularly preferred markers from this group are ones that have proven highly predictive of hemorrhagic transformation: namely, cellular fibronectin (c-Fn) and matrix metalloprotein-9 (MMP-9).

Those of ordinary skill in the art know that marker levels vary at certain time points; for example, the level of a marker may be at one level at three hours post-stroke event, and another level at nine hours post-stroke event. Thus when using multiple markers together which may or may not be correlated with each other it is necessary to provide interpretation through an algorithm that relates all markers together. This algorithm in current state of the art is a simple threshold level above which a marker is said to be indicative of an adverse event in the human body. A particular diagnosis and/or prognosis of said adverse event may depend upon the comparison of each marker to this value; alternatively, if only a subset of markers are outside of a normal range, then this subset may be indicative of a said adverse event.

Thus, in certain embodiments of the methods of the present invention, a plurality of markers are combined using an algorithm to increase the predictive value of the analysis in comparison to that obtained from the markers taken individually or in smaller groups. Most preferably, one or more markers for vascular damage, glial activation, inflammatory mediation, thrombosis, cellular injury, apoptosis, myelin breakdown, and specific and non-specific markers of cerebral injury are combined in a single assay to enhance the predictive value of the described methods. This assay is usefully predictive of multiple outcomes, for instance: determining whether or not a stroke occurred, then determining the subtype of stroke, then further predicting stroke prognosis. Moreover, different marker combinations in the assay may be used for different indications. Correspondingly, different algorithms interpret the marker levels as indicated on the same assay for different indications.

Preferred panels comprise markers for the following purposes: (1) diagnosis of stroke; (2) diagnosis of stroke mimics; (3) diagnosis of stroke and indication if an acute stroke has occurred; (4) diagnosis of stroke and indication if an non-acute stroke has occurred; (5) diagnosis of stroke, indication if an acute stroke has occurred, and indication if an non-acute stroke has occurred; (6) diagnosis of stroke and indication if an ischemic stroke has occurred; (7) diagnosis of stroke and indication if a hemorrhagic stroke has occurred; (8) diagnosis of stroke, indication if an ischemic stroke has occurred, and indication if a hemorrhagic stroke has occurred; (9) diagnosis of stroke and prognosis of a subsequent adverse outcome; (10) diagnosis of stroke and prognosis of a subsequent hemorrhagic transformation; (11) diagnosis of stroke, indication if a hemorrhagic stroke has occurred, and prognosis of a subsequent cerebral vasospasm; (12) diagnosis of stroke, indication if a hemorrhagic stroke has occurred, and further diagnosis of whether a subarachnoid hemorrhagic stroke has occurred; (13) diagnosis of stroke, indication if a ICH has occurred, and further diagnosis of likelihood of subsequent EHG.

In preferred embodiments, particular thresholds for one or more markers in a panel are not relied upon to determine if a profile of marker levels obtained from a subject are indicative of a particular diagnosis/prognosis. Rather, in accordance with the present invention, an evaluation of the entire profile is made by (1) first training an algorithm with marker information from samples from a test population and a disease population to which the clinical outcome of interest has occurred to determine weighting factors for each marker, and (2) then evaluating that result on a previously unseen population. Certain persons skilled in bioinformatics will recognize this procedure to be tantamount to the construction, and to the training, of a machine learning algorithm such as a neural network. The evaluation is determined by maximizing the numerical area under the ROC curve for the sensitivity of a particular panel of markers versus specificity for said panel at various individual marker levels. From this number, the skilled artisan can then predict a probability that a subject's current marker levels in said combination is indicative of the clinical marker of interest. For example, (1) the test population might consist solely of samples from a group of subjects who have had ischemic stroke and no other comorbid disease conditions, while (2) the disease population might consist solely of samples from a group of subjects who have had hemorrhagic stroke and no other comorbid disease conditions. A third, "normal" population might also be used to establish baseline levels of markers as well in a non-diseased population.

In preferred embodiments of the marker, and marker panel, selection methods of the present invention, the aforementioned weighting factors are multiplicative of marker levels in a nonlinear fashion. Each weighting factor is a function of other marker levels in the panel combination, and consists of terms that relate individual contributions, or independent and correlative, or dependent, terms. In the case of a marker having no interaction with other markers in regards to then clinical outcome of interest, then the specific value of the dependent terms would be zero.

The term "test sample" as used in this specification refers to a sample of bodily fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include blood, serum, plasma, cerebrospinal fluid, urine and saliva. In addition, one of skill in the art would realize that some test samples would be more readily analyzed following a fractionation or purification procedure, for example, separation of whole blood into serum or plasma components.

The term "markers of glial activation" as used in this specification refers to markers that indicate glial cell function. Glia mediate neuroendocrine and neuroimmune functions and are also important in synaptic remodeling and the loss of synaptic connections that occur during aging. These functions are carried out by changes in glia, including changes in shape, interactions with neurons and other glia, and gene expression. The predominant change that occurs in glia during aging is glial activation, which can progress to reactive gliosis in response to neurodegeneration. Markers distinguish normal and reactive glia. During aging, astrocytes hypertrophy and exhibit signs of metabolic activation, and astrocytic processes surround neurons. Microglia also become activated and subsets of activated microglial increase in number and may enter the phagocytic or reactive stage. Yet glial cells are intimately involved in the biochemical metabolic and neurotrophic support of the function of neurons, and glial actions at the synapses are crucial to normal neuronal transmission. Glia take up excess glutamate (which can be neurotoxic) and produce neurotrophic factors which keep cells alive, as well as interacting with other systems in transmitter-like actions. Thus, a loss of normal glial function could have dramatic impacts on normal neuronal function. Such specific markers of glial activation include, but are not limited to, GFAP, S100B, Mac-1, TLR4, TGF-β1 and CD14.

The term "markers of vascular damage" as used in this specification refers to markers that indicate endothelial damage. When the endothelium is damaged or becomes dysfunctional, a cascade leading to atherogenesis is precipitated, initiating a cycle of injury, immunologic induction, and amplification. Dysfunctional endothelium leads to increased permeability to lipoproteins and up-regulation of leukocyte and endothelial adhesion molecules. In response to the presence of certain activating substances, including oxidized LDL, monocyte chemotactic protein 1, interleukin (IL)-8, and platelet-derived growth factor (PDGF), leukocytes migrate into the wall of the artery. Such specific markers of vascular damage include, but are not limited to, c-Fn, MMP-9, endothelin-1 (ET-1), von Willebrand factor (vWf), and soluble (S−) adhesion molecules E-selectin, intercellular adhesion molecule-1 (ICAM-1), vascular cell adhesion molecule-1 (VCAM-1), plasma indexes of endothelial damage/dysfunction and soluble thrombomodulin (sTM).

The term "markers of inflammatory mediation" as used in this specification refers to markers that indicate an inflammatory response to a cerebral injury. Inflammatory responses are initiated and perpetuated by the interaction of immune cells with cells of the affected vessel wall. This is directed by a network of chemical messengers, which, in a state of vascular health, exist as balanced but opposing forces. These markers include various cytokines, proteases, adhesion molecules, and acute phase proteins as participants in the generation of vascular inflammation. Such specific markers of vascular damage include, but are not limited to, Cellular adhesion molecules such as Intracellular adhesion molecule-1, Vascular cellular adhesion molecule-1, NCAM and Selectins such as E-Selectin; Chemokines such as monocyte chemoattractant protein-1; Cytokines such as Interleukins 1, 1β, 1 receptor antagonist, 6, 8, 10, 18, transforming growth factor β, and Tumor necrosis factor-α; Proteases such as the matrix metalloproteinases MMP-9, MMP-3, and MMP-2; Accessory signaling markers such as CD40/CD40L; and acute phase proteins such as C-reactive protein, vascular endothelial growth factor, ceruloplasmin, fibrinogen, α1-acid glycoprotein, α1-antitrypsin, and haptoglobin.

The term "markers of thrombosis" as used in this specification refers to markers that indicate an coagulation event in ischaemic stroke. The blood clotting system is activated when blood vessels are damaged, exposing collagen, the major protein that connective tissue is made from. Platelets circulating in the blood adhere to exposed collagen on the cell wall of the blood vessel and secrete chemicals that start the clotting process as follows: Platelet aggregators cause platelets to clump together (aggregate). They also cause the blood vessels to contract (vasoconstrict), which reduces blood loss. Platelet aggregators include adenosine diphosphate (ADP), thromboxane A2, and serotonin (5-HT). Coagulants such as fibrin then bind the platelets together to form a permanent plug (clot) that seals the leak.

Fibrin is formed from fibrinogen in a complex series of reactions called the coagulation cascade. The enzymes that comprise the coagulation system are called coagulation factors, which are numbered in the order in which they were discovered. They include factor XII, factor XI, factor IX, factor X, factor VII, and factor V. The activation of the coagulation factors results in the formation of thrombin, which acts as a cofactor for the conversion of fibrinogen into fibrin. After the leak has been sealed with a blood clot, the body responds with another set of chemical messengers that oppose the actions of these chemicals. These include: Platelet aggregation inhibitors and vasodilators, such as nitric oxide and prostacyclin, which is also known as prostaglandin I2 (PGI2) Plasminogen activators that promote the breakdown of fibrin, such as tissue plasminogen activator (t-PA) Anticoagulants that inhibit enzymes in the coagulation cascade, such as antithrombin III (activated by heparin) and proteins C and S.

Such specific markers of thrombosis include, but are not limited to, von Willebrand factor, thrombin-antithrombin III complex, proteins C and S, tissue factor, fibrinopeptide A, plasmin-α-2-antiplasmin complex, prothrombin fragment 1+2, D-dimer, platelet factor 4, and β-thromboglobulin.

The term "marker of cellular injury and myelin breakdown" as used in this specification refers to markers associated with damage to the structural and functional molecules of the cell. Although any biologically important molecule in a cell can be the target of injury producing stress, four biochemical systems are particularly vulnerable: (1) the cell membrane, (2) energy metabolism, (3) protein synthesis, and (4) genes. Because many of the biochemical systems of the cell are inter-dependent, injury at one site typically leads to secondary injury to other cellular processes.

Myelin is the outer lipid rich (fatty) layer that covers nerves and nervous system pathways in the brain and spinal cord. The myelin sheath, a lipid-rich multilamellar membrane of relative stability, both insulates and enhances conduction in nerve axons. A notable feature of myelin-specific proteins, in particular myelin basic protein, is their susceptibility to proteolytic activity and their encephalitogenicity, which induces inflammatory demyelination in the CNS. The final common pathway of myelin breakdown in vivo is well documented and there is evidence that myelin disruption can be mediated directly by soluble (circulating) factors and for following receptor-driven phagocytosis by macrophages. However the exact mechanism(s) of demyelination in ischemic attack is still unresolved, both antigen-specific and—non-specific events having the potential to generate the myelinolytic process.

Cerebral injury leads to breakdown of the blood-brain barrier (BBB), exposing CNS antigens to the peripheral circulation and allowing the peripheral circulation access to the brain. The breakdown of the BBB leads to rapid acquisition of MBP-reactive T cell clones and Igs in stroke patients, but does not lead to autoimmune encephalitis. The degradation of myelin basic protein (MBP) by proteinase yields encephalitogenic peptides and its loss has been found to cause structural alteration of the myelin sheath. This suggests that MBP degradation is an initial step in the breakdown of myelin in demyelinating diseases. A calcium-activated neutral proteinase (calpain), which degrades MBP, was found to increase in activity in MS tissue and cerebrospinal fluid (CSF), and its presence in myelin suggests that myelin may be autodigested in demyelinating disease. The source of increased proteinase activity has been indicated as macrophages, lymphocytes, and proliferative astrocytes (reactive cells). Increased proteinase activity is found in Schwann cells in Wallerian degeneration, and the presence of calpain in myelin-forming oligodendrocytes and Schwann cells suggests that these cells are likely sources of degradative enzymes.

Such specific markers of cellular injury and myelin breakdown include, but are not limited to, creatinine phosphokinase brain band, tissue factor, Proteolipid protein, RU Malendialdehyde, calpain, and myelin basic protein.

The term "marker of apoptosis or growth factors" as used in this specification refers to markers involved in neuronal cell death. Numerous studies in experimental models of ischemia have now reported that apoptosis contributes to neuronal death (reviewed by Chalmers-Redman et al Mechanisms of nerve cell death: apoptosis or necrosis after cerebral ischemia. In: Green A R, Cross A J, eds. *Neuroprotective Agents and Cerebral Ischemia*. San Diego, Calif.: Academic Press; 1997:1-25.). Apoptosis requires the activation of a "cell death" gene program, and many of the extracellular signals that regulate apoptosis have been identified. For example, interaction between the Fas/APO-1 molecule, a cell surface protein, with its ligand (Fas-L) leads to programmed cell death. Soluble (s) Fas/APO-1, a molecule lacking the transmembrane domain of Fas/APO-1, blocks apoptosis by inhibiting interaction between Fas/APO-1 and Fas-L on the cell surface (see for instance Cheng J et al., Protection from Fas-mediated apoptosis by a soluble form of the Fas molecule. *Science*. 1994; 263:1759-1762.). Fas expression has been detected on B and T cells and on neutrophils. It has been suggested that the Fas/Fas-L pathway is one of the major mechanisms for T-cell-mediated cytotoxicity. It has also been demonstrated by in situ hybridization that the expression of Fas/APO-1 was induced in murine brain after transient global cerebral ischemia. Another gene product, bcl-2, has been shown to suppress apoptosis and to protect primary neuronal cell cultures from apoptosis induced by nerve growth factor depletion.

Macrophages and T lymphocytes kill target cells by inducing apoptosis, one of the potential mechanisms whereby the inflammatory cells invading the infarcted brain area participate in neuronal cell death. Stroke patients displayed an intrathecal production of proinflammatory cytokines, such as interleukin (IL)-1β, IL-6, IL-8, and granulocyte-macrophage colony-stimulating factor (GM-CSF), and of the anti-inflammatory cytokine IL-10 within the first 24 hours after the onset of symptoms, supporting the notion of localized immune response to the acute brain lesion in humans. Some of these cytokines (eg, IL-1β and IL-8) stimulate influx of leukocytes to the infarcted brain, a prerequisite for Fas/APO-1- and bcl-2-mediated apoptosis. TNF-α, a powerful cytokine inducing apoptosis in the extraneural compartment of the body, has been demonstrated to protect rat hippocampal, septal, and cortical cells against metabolic-excitotoxic insults and to facilitate regeneration of injured axons. More importantly, TNF-α and -β protect neurons against amyloid β-protein-triggered toxicity.

Other evidence demonstrates that apoptosis involves the activation of caspases, a unique family of structurally related, highly conserved, aspartate-specific, cysteine proteases that are necessary to carry out the signal for apoptotic cell death. Two members of the caspase family, caspase-1 and caspase-3, are known to cleave the most abundant caspase target substrate, actin. The 45-kDa actin is cleaved by caspase activation between Asp11 and Asn12 and between Asp244 and Gly245 to produce N-terminal 32-kDa fragments and C-terminal 15-kDa fragments. A polyclonal antibody to the last 5 amino acids of the C-terminus of the 32-kDa fragment of actin generated by caspase cleavage of intact actin has been developed and named "fractin" for "fragment of actin." Fractin labeling provides indirect evidence of caspase activation and demonstrates initiation of an apoptotic pathway, but does not rule out secondary necrosis. Other markers for apoptosis include biochemical evidence of oligointernucleosomal DNA fragmentation into approximately 180-bp multiples resulting from endonuclease activation that can be demonstrated with a typical "laddering" appearance on agarose gel electrophoresis. In addition, the terminal deoxynucleotidyl transferase-mediated dUTP-biotin nick end labeling (TUNEL) technique, which identifies 3'-OH ends of DNA-strand breaks, has been widely used as a marker of DNA damage or repair. However, the lack of specificity of TUNEL in detecting oligointernucleosomal DNA fragmentation precludes its use as a defining feature of apoptosis.

Such specific markers of apoptosis and growth factors include, but are not limited to, Brain natriuretic peptide, caspase 3, calbindin-D, heat shock protein 60 and 70, c-fos, c-jun, ubiquitin, and cytochrome C.

The term "specific marker of cerebral injury" as used in this specification refers to proteins or polypeptides that are associated with brain tissue and neural cells, and which can be correlated with a cerebral injury, but are not correlated with other types of injury. Such specific markers of cerebral injury include, but are not limited to, adenylate kinase, brain-derived neurotrophic factor, calbindin-D, lactate dehydrogenase, myelin basic protein, neural cell adhesion molecule, neuron-specific enolase, neurokinin A, neurokinin B, neurotensin, neurotrophin-3, neurotrophin-4/5, neuropeptide Y, proteolipid protein, substance P, thrombomodulin, and protein kinase C gamma.

The term "non-specific marker of cerebral injury" as used in this specification refers to proteins or polypeptides that are elevated in the event of cerebral injury, but may also be elevated due to non-cerebral events. Non-specific markers include, but are not limited to, ApoC-I and ApoC-II, A-type natriuretic peptide, B-type natriuretic peptide, C-type natriuretic peptide, adrenomedullin, β-thromboglobulin, C-reactive protein, Cardiac Troponin I and Troponin T, Creatine kinase MB, D-dimer, E-selectin, endothelin-1, endothelin-2, and endothelin-3, A-, F-, and H-Fatty acid binding protein, fibrinopeptide A, hemoglobin $\alpha_2$, chain head activator, insulin-like growth factor-1, MMP-3, plasmin-α-2-antiplasmin complex, platelet factor 4, 8-epi PGF sub(2α), PGI2, PGE2, prothrombin fragment 1+2, thrombin-antithrombin III complex, tissue factor, transforming growth factor β, and von Willebrand factor.

The term "diagnosis", as used in this specification refers to predict the type of disease or condition from a set of marker values and/or patient symptoms. This is in contrast to disease prediction, which is to predict the occurrence of disease before it occurs, and the term "prognosis", which is to predict disease progression at a future point in time from one or more indicator value(s) at a previous point in time.

The term "correlating," as used in this specification refers to a process in which a set of examples of clinical inputs from subjects, such as marker levels, and their corresponding outputs, such as whether a subject suffered from a specific type of stroke, are related to each other. This relationship can be determined by comparing such examples to examples from a control and/or disease-free population at a later point in time, and selecting those indicators which can differentiate between the two disease states as a function of time alone or in combination at a certain probability level. The selection process is described herein. The selected markers, each at a certain level range which might be a simple threshold, are said to be correlative or associative with one of the disease states. Said correlated markers can be then be used for disease detection, diagnosis, prognosis and/or treatment outcome. Preferred methods of correlating markers is by performing marker selection by a feature selection algorithm and classification by mapping functions described herein. A preferred probability level is a 3% chance, 5% chance, a 7% chance, a 10% chance, a 15% chance, a 20% chance, a 25% chance, a 30% chance, a 35% chance, a 40% chance, a 45% chance, a 50% chance, a 55% chance, a 60% chance, a 65% chance, a 70% chance, a 75% chance, a 80% chance, a 85% chance, a 90% chance, a 95% chance, and a 100% chance. Each of these values of probability is plus or minus 2% or less. A preferred threshold level for markers of the present invention is about 25 pg/mL, about 50 pg/mL, about 60 pg/mL, about 75 pg/mL, about 100 pg/mL, about 150 pg/mL, about 200 pg/mL, about 300 pg/mL, about 400 pg/mL, about 500 pg/mL, about 600 pg/mL, about 750 pg/mL, about 1000 pg/mL, and about 2500 pg/mL. The term "about" in this context refers to +/−10%.

In yet another of its aspects, the present invention is embodied in methods for determining a treatment regimen for use in a patient diagnosed with stroke. The methods preferably comprise determining a level of one or more diagnostic or prognostic markers as described herein, and using the markers to determine a diagnosis for a patient. For example, a prognosis might include the development or predisposition to delayed neurologic deficits after stroke onset. One or more treatment regimens that improve the patient's prognosis by reducing the increased disposition for an adverse outcome associated with the diagnosis can then be used to treat the patient. Such methods may also be used to screen pharmacological compounds for agents capable of improving the patient's prognosis as above.

In yet another of its aspect, the present invention relates to methods of identifying a patient at risk for m-MCA or EHG after ICH. Such methods preferably comprise comparing an amount of a marker predictive of a subsequent m-MCA or EHG after ICH, said marker selected from the group consisting of cellular fibronectin (c-Fn), and matrix metalloprotease-9 (MMP-9), in a test sample from a patient diagnosed with an acute stroke to a predictive level of said marker, wherein said patient is identified as being at risk for m-MCA or EHG after ICH by a level of said marker equal to or greater than said predictive level.

In yet another of its aspects, the present invention is embodied in methods of differentiating ischemic stroke from hemorrhagic stroke using such marker combination panels.

In yet another of its aspects, the present invention Is embodied in kits for determining the diagnosis or prognosis of a patient. These kits preferably comprise devices, software and reagents for measuring one or more marker levels in a patient sample, and instructions for performing the assay. Additionally, the kits contain a computer software program to be run on a computer or other means for converting marker level(s) to a prognosis. Such kits preferably contain sufficient reagents to perform one or more such determinations, and are standardized to run on an instrument used to analyze blood samples, such as Abbott Laboratories' AxSYM®, Roche Diagnostics' Cardiac Reader®, or Dade Behring's Stratus® CS Analyzer.

DETAILED DESCRIPTION OF THE INVENTION

In accordance with the present invention, there are provided methods and apparatus for the identification and use of a panel of markers for the prediction of m-MCA and/or EHG after ICH.

Fibronectins are adhesive dimeric glycoproteins that promote cell-cell and cell-matrix interactions (see for instance Hynes R O. Fibronectins. *Sci Am*. 1986; 254: 42-51.). Plasma fibronectin (p-Fn) is primarily produced by hepatocytes, but plasma also contains small quantities of cellular fibronectin (c-Fn), which is mainly synthesized by endothelial cells (see for instance Peters J H, Sporn L A, Ginsberg M H, Wagner D D. Human endothelial cells synthesize, process, and secrete fibronectin molecules bearing an alternatively spliced type II homology (ED1). *Blood*. 1990; 75:1801-1808.). Because c-Fn is largely confined to the vascular endothelium, high plasma levels of this molecule might be indicative of endothelial damage. In fact, plasma c-Fn levels have been reported to be increased in patients with vascular injury secondary to vasculitis, sepsis, acute major trauma, and diabetes, (see for instance Peters J H, Maunder R J, Woolf A D, Cochrane G H, Ginsberg M H. Elevated plasma levels of ED1_ ("cellular") fibronectin in patients with vascular injury. *J Lab Clin Med*. 1989; 113:586-597; Kanters S D, Banga J D, Algra A, Frijns R C, Beutler J J, Fijnheer R. Plasma levels of cellular fibronectin in diabetes. *Diabetes Care*. 2000; 24:323-327.). Since HT after cerebral ischemia seems to be the result of the continuous disappearance of basal membrane components (see for instance Hamann G F, Okada Y, del Zoppo G J. Hemorrhagic transformation and microvascular integrity during focal cerebral ischemia/reperfusion. *J Cereb Blood Flow Metab*. 1996; 16:1373-1378.), in the instant invention we show high levels of plasma c-Fn are associated with m-MCA. We also show elevation in patients with ICH who had subsequent EHG for the first time.

Because the mortality rate of m-MCA is 80%, and those who do survive experience severe neurological deficits, the identification of factors that can predict secondary brain edema is of critical importance. The instant invention demonstrates that plasma c-Fn levels in patients experiencing MCA are significantly higher in patients in which m-MCA evolves and teaches that c-Fn levels >16.6 µg/mL can predict the development of m-MCA with a sensitivity and negative predictive value of 100%. Therefore, c-Fn is a useful marker of those patients who are at greatest risk for m-MCA.

In addition, as ICH has a 30-50% mortality rate, half of this coming from continued bleeding, identification of markers of such bleeds is also of critical importance to change treatment outcomes. The instant invention demonstrates that plasma c-Fn levels in patients experiencing ICH are significantly higher in patients in which EHG evolves and teaches that c-Fn levels >6 µg/mL can predict the development of EHG with a sensitivity and negative predictive value of 100%. Therefore, c-Fn is a useful marker of those patients who are at greatest risk for EHG after ICH.

The loss of microvascular integrity secondary to the continuous disappearance of the antigens of the endothelial components has been reported as being responsible for hemorrhagic transformation after ischemic injury (Castellanos et al 2004). Among these antigens, c-Fn is especially important because it mediates the interaction between the endothelium and blood cells as well as other blood components. Moreover, Fn plays an important role in blood clot formation by mediating the adhesion of platelets to fibrin (see for instance Hynes R O. Fibronectins. *Sci Am*. 1986; 254:42-51.), so the disappearance of the c-Fn of the vascular endothelium secondary to ischemia might damage this clotting mechanism, facilitating additional bleeding events. Although high c-Fn levels have been previously reported in patients with ischemic stroke, no previous data are available on the association between c-Fn levels in patients with acute ischemic stroke.

The increase of vascular permeability and subsequent extravasation of serum components leading to EHG after ICH may be the result of several mechanisms including the activation of MMPs, which is secondary to ischemia. The instant invention also details the significant association between MMP-9 levels and EHG after ICH and in a nonselected series of stroke patients who experience ICH. However, the fact that c-Fn is almost exclusively located at the endothelium suggests that this molecule could be a more specific marker of a high risk for EHG. This hypothesis is supported by our finding that c-Fn levels, but not MMP-9 levels, remained independently associated with EGH in the logistic regression analysis. Moreover, plasma IL-6 levels >24 pg/mL conveyed a 16-fold risk for the development of EHG after controlling for other markers of inflammation.

The relationship between an increased inflammatory reaction and EHG might be caused by the disappearance of the basal lamina components, such as c-Fn, laminin, and collagen IV, and by the loss of microvascular integrity in the tissue around the hematoma caused by the activation of matrix metalloproteinases (see for instance Lee K R, Kawai N, Seoung K, Sagher O, Hoff J T. Mechanisms of edema formation after intracerebral hemorrhage: effects of thrombin on cerebral blood flow, blood brain barrier permeability and cell survival in a rat model. *J. Neurosurg*. 1997; 86:272-278; Horstmann S, Kalb P, Koziol J, Gardner H, Wagner S. Profiles of matrix metalloproteinases, their inhibitors, and laminin in stroke patients. Influence of different therapies. *Stroke*. 2003; 34:2165-2172.). In this context, both MMP-9 and c-Fn concentrations in blood were significantly higher in patients with EHG, and c-Fn was the most powerful predictor of ICH enlargement. Plasma c-Fn levels >6 µg/mL were associated with 92-fold increase in the risk of EHG, and c-Fn levels showed a high correlation with the percentage of the ICH growth. Because c-Fn is largely confined to the vascular endothelium (see for instance Vartio T, Laitinen L, Narvanen O, Cutolo M, Thornell L E, Zardi L, Virtanen I. Differential expression of the ED sequence-containing form of cellular fibronectin in embryonic and adult human tissues. *J Cell Sci.* 1987; 88:419-430.), high plasma levels of this molecule might be indicative of endothelial damage. In fact, plasma c-Fn levels have been reported to be increased in patients with vascular injury secondary to vasculitis, sepsis, acute major trauma, and diabetes, and in patients with ischemic stroke (see for instance Kanters S D, Banga J D, Algra A, Frijns R C, Beutler J J, Fijnheer R. Plasma levels of cellular fibronectin in diabetes. *Diabetes Care.* 2000; 24:323-327.). In addition, c-Fn plays an important role in blood clot formation by mediating the adhesion of platelets to fibrin, so the disappearance of the c-Fn of the vascular endothelium might damage this clotting mechanism, facilitating ICH enlargement. However, the synthesis of c-Fn may also be triggered during inflammatory processes by agents such as transforming growth factors and leukocytes (La Fleur M, Beaulieu A D, Kreis C, Poubelle P. Fibronectin gene expression in polymorphonuclear leukocytes. Accumulation of mRNA in inflammatory cells. *J Biol Chem.* 1987; 262:2111-2115; Roberts C J, Birkenmeier T M, McQuillan J J et al. Transforming growth factor α stimulates the expression of fibronectin and of both subunits of the human fibronectin receptor by cultured human lung fibroblasts. *J Biol Chem.* 1988; 263:4586-4592.).

The basal lumina disruption and the subsequent release of c-Fn after brain ischemic injury into the plasma, as well as accelerated Fn synthesis by endothelial cells and other cells such as polymorphonuclear leukocytes arriving at the ischemic tissue as part of the ischemic inflammatory cascade, could be among the participating mechanisms. Interleukins and transforming growth factor, whose expression is increased as a result of ischemia (see for instance Feuerstein G Z, Wang X, Barone F C. Inflammatory mediators and brain injury: the role of cytokines and chemokines in stroke and CNS diseases. In: Ginsberg Md., Bogousslavsky J, eds. *Cerebrovascular Disease:Pathophysiology, Diagnosis, and Management.* Boston, Mass.: Blackwell Science; 1998:507-531.), have been shown to stimulate Fn synthesis (see for instance Roberts C J, Birkenmeier T M, McQuillan J J, Akiyama S K, Yamada S S, Chen W T, Yamada K M, McDonald J A. Transforming growth factor beta stimulates the expression of fibronectin and of both subunits of the human fibronectin receptor by cultured human lung fibroblast. *J Biol. Chem.* 1988; 263:4586-4592.). Increased c-Fn synthesis could be an attempt to decrease endothelial destruction by MMPs, which might explain the positive correlation between c-Fn and MMP-9 in the instant invention.

Recently, many researchers have investigated the possibility of blood-borne markers of stroke and its subtypes. This approach is well established in the clinical setting of suspected myocardial ischemia. In acute coronary syndromes, the myocardial isoform of creatinine phosphokinase and troponin play an important role both in treatment decisions and clinical research. Similarly, B-type natriuretic peptide has become a routine part of the assessment of patients with congestive heart failure and dyspnea. However, the ischemic cascade of glial activation and ischemic neuronal injury in stroke is far more complex than myocardial ischemia and less amenable to the use of a single biochemical marker. Indeed, the authors of the instant invention know of no individual biochemical marker has been demonstrated to possess the requisite sensitivity and specificity to allow it to function independently as a clinically useful diagnostic marker for stroke, stroke mimic, ischemic/hemorrhagic differentation, and/or transient ischemic attacks.

Thus a panel of markers was envisioned to overcome this deficiency in 1998 or earlier for detecting stroke (see for instance Misz M, Olah L, Kappelmayer J, Blasko G, Udvardy M, Fekete I, Csepany T, Ajzner E, Csiba L. Hemostatic abnormalities in ischemic stroke, Orv Hetil. 1998 Oct. 18; 139(42): 2503-7; Tarkowski E, Rosengren L, Blomstrand C, Jensen C, Ekholm S, Tarkowski A. Intrathecal expression of proteins regulating apoptosis in acute stroke. *Stroke.* 1999 February; 30(2):321-7; Stevens H, Jakobs C, de Jager A E, Cunningham R T, Korf J. Neurone-specific enolase and N-acetyl-aspartate as potential peripheral markers of ischaemic stroke. *Eur J Clin Invest.* 1999 January; 29(1):6-11.) or its sub-types (see for instance Soderberg S, Ahren B, Stegmayr B, Johnson O, Wiklund P G, Weinehall L, Hallmans G, Olsson T. Leptin is a risk marker for first-ever hemorrhagic stroke in a population-based cohort. *Stroke.* 1999 February; 30(2):328-37).

In many studies since this time, many blood-borne proteomic markers have been shown to be associated with stroke and its sub-types. For example, acute stroke has been associated with serum elevations of numerous inflammatory and anti-inflammatory mediators such as interleukin 6 (IL-6) and matrix metalloproteinase-9 (MMP-9) (see for instance Kim J S, Yoon S S, Kim Y H, Ryu J S. Serial measurement of interleukin-6, transforming growth factor-beta, and S-100 protein in patients with acute stroke. *Stroke.* 1996; 27:1553-1557; Dziedzic T, Bartus S, Klimkowicz A, Motyl M, Slowik A, Szczudlik A. Intracerebral hemorrhage triggers interleukin-6 and interleukin-10 release in blood. *Stroke.* 2002; 33:2334-2335; Beamer N B, Coull B M, Clark W M, Hazel J S, Silberger J R. Interleukin-6 and interleukin-1 receptor antagonist in acute stroke. *Ann Neurol.* 1995; 37:800-805; Montaner J, Alvarez-Sabin J, Molina C, et al. Matrix metalloproteinase expression after human cardioembolic stroke: temporal profile and relation to neurological impairment. *Stroke.* 2001; 32:1759-1766; Perini F, Morra M, Alecci M, Galloni E, Marchi M, Toso V. Temporal profile of serum anti-inflammatory and pro-inflammatory interleukins in acute ischemic stroke patients. *Neurol Sci.* 2001; 22:289-296; Vila N, Castillo J, Davalos A, Chamorro A. Proinflammatory cytokines and early neurological worsening in ischemic stroke. *Stroke.* 2000; 31: 2325-2329), markers of impaired hemostasis and thrombosis (see for instance Fon E A, Mackey A, Cote R, et al. Hemostatic markers in acute transient ischemic attacks. *Stroke.* 1994; 25:282-286; Takano K, Yamaguchi T, Uchida K. Markers of a hypercoagulable state following acute ischemic stroke. *Stroke.* 1992; 23:194-198.), and markers of glial activation such as S100b (see for instance Buttner T, Weyers S, Postert T, Sprengelmeyer R, Kuhn W. S-100 protein: serum marker of focal brain damage after ischemic territorial MCA infarction. *Stroke.* 1997; 28:1961-1965; Martens P, Raabe A, Johnsson P. Serum S-100 and neuron-specific enolase for prediction of regaining consciousness after global cerebral ischemia. *Stroke.* 1998; 29:2363-2366.). Several of these mediators, including IL-6, have been shown to be elevated within hours after ischemia and correlate with infarct volume (see for instance Fassbender K, Rossol S, Kammer T, et al. Proinflammatory cytokines in serum of patients with acute cerebral ischemia: kinetics of secretion and relation to the extent of brain damage and outcome of disease. *J Neurol Sci.* 1994; 122:135-139; Tarkowski E, Rosengren L, Blomstrand C, et al. Early intrathecal production of interleukin-6 predicts the size of brain lesion in stroke. *Stroke.* 1995; 26: 1393-1398).

Other authors have looked at the differentiation between TIA and stroke (see for instance Dambinova S A, Khounteev G A, Skoromets A A. Multiple panel of biomarkers for TIA/ stroke evaluation. *Stroke*. 2002; 33:1181-1182.) or type of hemorrhage (see for instance McGirt M J, Lynch J R, Blessing R, Warner D S, Friedman A H, Laskowitz D T. Serum von Willebrand factor, matrix metalloproteinase-9, and vascular endothelial growth factor levels predict the onset of cerebral vasospasm after aneurysmal subarachnoid hemorrhage. *Neurosurgery*. 2002; 51:1128-1134).

To this date, most of these studies have been in small number of patients and while have individual markers in common, the panels proposed in each have not been replicated. This is due to the fact that many reported panels merely linearly add the effects of multiple markers, or perform simple logistic regression to get correlative effects of a panel. One such example of the current state of the art is that of Reynolds et al. (Mark A. Reynolds, Howard J. Kirchick, Jeffrey R. Dahlen, Joseph M. Anderberg, Paul H. McPherson, Kevin K. Nakamura, Daniel T. Laskowitz, Gunars E. Valkirs, and Kenneth F. Buechler, Early biomarkers of stroke, *Clinical Chemistry* 49:10 1733-1739, 2003). In this paper, a five marker panel consisting of S-100β, B-type neurotrophic growth factor, von Willebrand factor, matrix metalloproteinase-9, and monocyte chemotactic protein-1 was disclosed as suggested blood-borne panel to diagnosis acute ischemic stroke. In this analysis, univariate analysis was used to select an initial pool of candidate markers, and then multivariate analysis was used to achieve the final panel. However, as shown in the instant invention, this methodology is flawed. The result of this paper was tested on data used to train such, a typical mistake which usually leads to an irreproducible result.

Another example of the state of the art is U.S. patent application Ser. No. 10/673,077 and/or U.S. patent Ser. No. 10/225,082. In these application, a variety of markers for the diagnosis of stroke are envisioned, the mere presence or absence of such markers in the blood being indicative of disease. This methodology is fatally flawed, however, since it does not indicate how to relate the collective nonlinear effects of all markers to the outcome of interest, i.e. specify an algorithm to select among such markers and another to classify such markers as related to outcome. Instead, the application anticipates using the thresholded values of such markers as an indicator, giving a simple binary response of each as a value. As such markers are all treated as independent variables, there is no interaction between them, another fatal flaw.

Most existing statistical and computational methods for biomarker feature selection, such as U.S. patent application Ser. Nos. 10/673,077 and/or U.S. patent application Ser. No. 10/714,078, have focused on differential expression of markers between diseased and control data sets. This metric is tested by simple calculation of fold changes, by t-test, and/or F test. These are based on variations of linear discriminant analysis (i.e., calculating some or the entire covariance matrix between features).

However, the majority of these data analysis methods are not effective for biomarker identification and disease diagnosis for the following reasons. First, although the calculation of fold changes or t-test and F-test can identify highly differentially expressed biomarkers, the classification accuracy of identified biomarkers by these methods, is, in general, not very high. This is because linear transforms typically extract information from only the second-order correlations in the data (the covariance matrix) and ignore higher-order correlations in the data. For such cases, nonlinear transforms are necessary. Second, most scoring methods do not use classification accuracy to measure a biomarker's ability to discriminate between classes. Therefore, biomarkers that are ranked according to these scores may not achieve the highest classification accuracy among biomarkers in the experiments. Even if some scoring methods, which are based on classification methods, are able to identify biomarkers with high classification accuracy among all biomarkers in the experiments, the classification accuracy of a single marker cannot achieve the required accuracy in clinical diagnosis. Third, a simple combination of highly ranked markers according to their scores or discrimination ability is usually not be efficient for classification, as shown in the instant invention. If there is high mutual correlation between markers, then complexity increases without much gain.

Accordingly, the instant invention provides a methodology that can be used for biomarker feature selection and classification, and is applied in the instant application to detection of stroke and its subtypes.

Exemplary Biomarkers related to detection and prediction of adverse stroke outcomes.

A comprehensive methodology for identification of one or more markers for the prognosis, diagnosis, and detection of disease has been described previously. Suitable methods for identifying such diagnostic, prognostic, or disease-detecting markers are described in detail in U.S. Pat. No. 6,658,396, U.S. patent application Ser. No. 09/611,220, entitled NEURAL-NETWORK-BASED INDENTIFICATION, AND APPLICATION, OF GENOMIC INFORMATION PRACTICALLY RELEVANT TO DIVERSE BIOLOGICAL AND SOCIOLOGICAL PROBLEMS, filed Jul. 6, 2000, and U.S. provisional patent application Ser. No. 11/046,592, entitled CELLULAR FIBRONECTIN AS A DIAGNOSTIC MARKER OF STROKE AND METHODS OF USE THEREOF, filed Jan. 29, 2005, each of which patents and relevant applications is hereby incorporated by reference in its entirety, including all tables, figures, and claims. Briefly, our method of predicting relevant markers given an individual's test sample is an automated technique of constructing an optimal mapping between a given set of input marker data and a given clinical variable of interest. We illustrate this method, as well as additional marker descriptions, further in the U.S. provisional patent application Ser. No. 11/046,592.

We first obtain patient test samples of some bodily fluid, such as blood, cerebrospinal fluid, or urine from two or more groups of patients. Preferred fluid is blood. The patients are those exhibiting symptoms of a disease event, say stroke, which is determined at a later time, and those not exhibiting the same disease event, which are viewed as controls, though these patients might have another disease event distinct from the first. Samples from these patients are taken at various time periods after the event has occurred, and assayed for various markers as described within. Clinical information, such as sex, age, time from onset of symptoms to treatment, NIHSS score, biochemistry and vital signs at admission, and neuroimaging findings are collected at various time periods. Preferred time periods for the instant invention include 0, 3 hours, 6 hours, 9 hours, 12 hours, 15 hours, 18 hours, 24 hours, 36 hours, 48 hours, 72 hours, 1 week, 2 weeks, 3 weeks, 4 weeks, 3 months and 6 months. Time is measured either from onset of symptoms of admission into a clinical setting where the patient receives care. This marker and clinical information form a set of examples of clinical inputs and their corresponding outputs, the outputs being the clinical outcome of interest, for instance stroke and stroke subtype occurrence or non-occurrence, EHG or m-MCA prediction, or stroke mimic subtype. These quantities are as described in the Introduction.

We then use an algorithm to select the most relevant clinical inputs that correspond to the outcome for each time period. This process is also known as feature selection. In this process, the minimum number of relevant clinical inputs that are needed to fully differentiate and/or predict disease prognosis, diagnosis, or detection with the highest sensitivity and specificity are selected for each time period. The feature selection is done with an algorithm that selects markers that differentiate between patient disease groups, say hemorrhagic versus ischemic. The relevant clinical input combinations might change at different time periods, and might be different for different clinical outcomes of interest.

We then train a classifier to map the selected relevant clinical inputs to the outputs. A classifier assigns relative weightings to individual marker values. We note that the construct of a classifier is not crucial to our method. Any mapping procedure between inputs and outputs that produces a measure of goodness of fit, for example, maximizing the area under the receiver operator curve of sensitivity versus 1-specificity, for the training data and maximizes it with a standard optimization routine on a series of validation sets would also suffice.

Once the classifer is trained, it is ready for use by a clinician. The clinician enters the same classifer inputs used during training of the network by assaying the selected markers and collecting relevant clinical information for a new patient, and the trained classifier outputs a maximum likelihood estimator for the value of the output given the inputs for the current patient. The clinician or patient can then act on this value. We note that a straightforward extension of our technique could produce an optimum range of output values given the patient's inputs as well as specific threshold values for inputs.

One versed in the ordinary state of the art knows that many other markers in the literature once measured from the blood in a diseased and healthy patient, selected through use of an feature selection algorithm might be diagnostic of cardiovascular events if measured in combination with others and evaluated together with a nonlinear classification algorithm. We describe some of these other markers, previously considered for diagnosis or prognosis of cardiovascular events and thus not novel in themselves. This list is meant to serve as illustrative and not meant to be exhaustive. Selected marker descriptions in the following list are similar to U.S. patent application Ser. No. 10/673,077 and/or U.S. patent application Ser. No. 10/714,078, both of which are noted as prior art. However, the instant invention goes beyond what is taught or anticipated in these applications, providing a rigorous methodology of discovering which representative markers are best suited to building a predictive model for determining a clinical outcome and building a model for interpolating between such markers to determine clinical outcome, while the methodology described in U.S. patent application Ser. No. 10/673,077 and/or U.S. patent application Ser. No. 10/714,078 rely on simple linear relationships between markers and linear optimization techniques to find them. As also previously discussed in the instant invention, neither the general markers used, the idea of combinations of such markers, nor techniques used to analyze them are novel.

Blood pressure regulatory markers—Natriuretic peptides

The following are exemplary markers related to blood pressure regulation. This list is not meant to be limiting.

B-type natriuretic peptide (BNP), also called brain-type natriuretic peptide is a 32 amino acid, 4 kDa peptide that is involved in the natriuresis system to regulate blood pressure and fluid balance. See for instance Bonow, R. O., Circulation 93:1946-1950 (1996). The precursor to BNP is synthesized as a 108-amino acid molecule, referred to as "pre pro BNP," that is proteolytically processed into a 76-amino acid N-terminal peptide (amino acids 1-76), referred to as "NT pro BNP" and the 32-amino acid mature hormone, referred to as BNP or BNP 32 (amino acids 77-108). It has been suggested that each of these species NT pro-BNP, BNP-32, and the pre pro BNP—can circulate in human plasma. See for instance Tateyama et al., Biochem. Biophys. Res. Commun. 185: 760-7 (1992); Hunt et al., Biochem. Biophys. Res. Commun. 214: 1175-83 (1995). The 2 forms, pre pro BNP and NT pro BNP, and peptides which are derived from BNP, pre pro BNP and NT pro BNP and which are present in the blood as a result of proteolyses of BNP, NT pro BNP and pre pro BNP, are collectively described as markers related to or associated with BNP.

The term "BNP" as used herein refers to the mature 32-amino acid BNP molecule itself. As the skilled artisan will recognize, however, because of its relationship to BNP, the concentration of NT pro-BNP molecule can also provide diagnostic or prognostic information in patients. The phrase "marker related to BNP or BNP related peptide" refers to any polypeptide that originates from the pre pro-BNP molecule, other than the 32-amino acid BNP molecule itself. Proteolytic degradation of BNP and of peptides related to BNP have also been described in the literature and these proteolytic fragments are also encompassed it the term "BNP related peptides."

BNP and BNP-related peptides are predominantly found in the secretory granules of the cardiac ventricles, and are released from the heart in response to both ventricular volume expansion and pressure overload. See for instance Wilkins, M. et al., Lancet 349: 1307-10 (1997). Elevations of BNP are associated with raised atrial and pulmonary wedge pressures, reduced ventricular systolic and diastolic function, left ventricular hypertrophy, and myocardial infarction. See for instance Sagnella, G. A., Clinical Science 95: 519-29 (1998). Furthermore, there are numerous reports of elevated BNP concentration associated with congestive heart failure and renal failure.

Endothelin-1 (ET-1) is a 21 aminoacid peptide with potent vasoconstrictor properties. It is synthesised and released by endothelial cells in both the peripheral and cerebral vasculature and is also localised within neurones in discrete brain areas where it may contribute to the central regulation of blood pressure. It has been shown that intracisternal ET-1 in conscious rats induces a marked pressor response that is associated with an intense widespread reduction in cerebral blood flow. Subsequent studies with local application of ET-1 to the middle cerebral artery (MCA) revealed a dose dependent reversible vasoconstriction of the artery that resulted in profound reductions in local cerebral blood flow and the development of cerebral infarction. Thus abluminal application of ET-1 to the MCA offers a simple model of reversible focal cerebral ischaemia in the rat that complements the existing models of permanent MCA occlusion. Many authors have shown that ischemic stroke is associated with elevated plasma ET-1 levels (For instance see Ziv I et al, Increased plasma endothelin-1 in acute ischemic stroke. Stroke. 1992 July; 23(7):1014-6.). Elevation of ET-1 in plasma has been reported 1 to 3 days after ischemic stroke (Lampl et al. Endothelin in cerebrospinal fluid and plasma of patients in the early stage of ischemic stroke. Stroke. 1997 October; 28(10):1951-5). Related to ET-1 is endothelin-2 and endothelin-3, which are also 21 amino acid residues in length, and are produced by hydrolysis of big endothelin-2 and big endothelin-3, respectively (Yap et al., Br. J. Pharmacol. 129:170-6, 2000; Lee et al., Blood 94:1440-50, 1999).

Hemostatic Markers

The following are exemplary markers related to hemostasis. This list is not meant to be limiting.

D-Dimer

D-dimer is a fibrin degradation product with an approximate molecular mass of 200 kDa. D-dimer marks plasmin activity and fibrinolysis, including stroke. Normal plasma levels of D-Dimer are <150 ng/ml (750 pM). D-dimer levels in ischemic stroke have been reported as being high in all phases [N. Ono, T. Koyama, A. Suchiro, K. Oku, K. Fujikake and E. Kakishita, Clinical significance of new coagulation and fibrinolytic markers in ischemic stroke patients. *Stroke* 22 (1991), pp. 1369-1373. and M. Yamazaki, S. Uchiyama and S. Maruyama, Alterations of haemostatic markers in various subtypes and phases of stroke. *Blood Coagulation and Fibrinolysis* 4 (1993), pp. 707-712], significantly high in subacute and chronic phases [H. Tohgi, M. Kawashima, K. Tamura and H. Suzuki, Coagulation-fibrinolysis abnormalities in acute and chronic phases of cerebral thrombosis and embolism. *Stroke* 21 (1990), pp. 1663-1667.], and high in acute phase but low in chronic phase [M. Fisher and R. Francis, Altered coagulation in cerebral ischemia. Platelet, thrombin and plasmin activity. *Arch Neurol* 47 (1990), pp. 1075-1079].

Stroke subtype is not the only factor that might influence the concentration of hemostatic markers. Coagulation and fibrinolysis may also be altered by drugs and associated diseases such as angina, atrial fibrillation, and diabetes mellitus.

Thrombin is a multifunctional serine protease that is involved not only in mediating the cleavage of fibrinogen to fibrin in the coagulation cascade but also in activating a variety of cell types, including platelets and endothelial cells. Thrombin signaling in the endothelium might result in a multitude of phenotypic changes, including alterations in cell shape, permeability, vasomotor tone, leukocyte trafficking, migration, DNA synthesis, angiogenesis, and hemostasis. Thrombin signaling in the endothelium is mediated by a family of 7-transmembrane G protein-coupled receptors, termed protease-activated receptors (PARs). Currently, 4 members of the PAR family have been identified (PAR-1 through PAR-4;). PAR-1 and PAR-3 are thrombin receptors. Thrombin activation of PAR-4 requires PAR-3 as a thrombin-binding cofactor. Human umbilical vein endothelial cells (HUVECs) have been reported to express PAR-1, PAR-2, and, to a lesser extent, PAR-3, but not PAR-4. One study provided evidence for the existence of functional PAR-4 receptors (as well as those for PAR-1 and PAR-2 but not PAR-3) in the endothelium of human coronary artery ring segments. Of the various PAR family members, PAR-1 is the predominant thrombin receptor in endothelial cells. Thrombin activates PAR-1 by binding to a unique site in the extracellular domain of the receptor, resulting in cleavage between Arg41 and Ser42 and consequent exposure of a new N-terminus. The unmasked tethered ligand (SFLLRN) interacts with the extracellular loop 2 of the receptor (amino acids 248 to 268), resulting in receptor activation. Once activated, PAR-1 is coupled to a family of heterotrimeric G proteins, consisting of an -subunit and a β-dimer. The G proteins are in turn linked to a number of signal intermediates that include, but are not limited to, mitogen-activated protein kinase (MAPK), protein kinase C (PKC), phosphatidyl inositol 3-kinase (PI3K), and Akt. Thrombin signaling might result in posttranscriptional changes, including calcium influx, cytoskeletal reorganization, and release of soluble mediators, growth factors, and matrix metalloproteinases. In addition, thrombin signaling results in changes in downstream gene transcription. For example, under in vitro conditions, thrombin has been shown to increase the expression of genes that are involved in cell proliferation, inflammation, leukocyte adhesion, vasomotor tone, and hemostasis.

Thrombin-antithrombin III complex (TAT) regulates thrombin, factor XIa, factor XIIa, and factor IXa proteolytic activity. TAT is formed immediately following thrombin activation in the presence of heparin, which is the limiting factor in this interaction. Heparin enhances the inhibitory activity of ATIII by 2-3 orders of magnitude, resulting in almost sudden inactivation of proteinases inhibited by ATIII. ATIII inhibits its target proteinases through the formation of a covalent 1:1 stoichiometric complex. The normal plasma concentration of the approximately 100 kDa TAT is <5 ng/ml (50 pM). TAT concentration is elevated in patients with acute myocardial infarction and unstable angina, especially during spontaneous ischemic episodes (Biasucci, L. M. et al., Am. J. Cardiol. 77:85-87, 1996; Kienast, J. et al., Thromb. Haemost. 70:550-553, 1993). Elevation of the plasma TAT concentration is also seen in any condition associated with coagulation activation, including stroke, surgery, trauma, disseminated intravascular coagulation, and thrombotic thrombocytopenic purpura. TAT has a half-life of approximately 5 minutes in the bloodstream (Biasucci, L. M. et al., Am. J Cardiol. 77:85-87, 1996). TAT concentration is elevated in, exhibits a sharp drop after 15 minutes, and returns to baseline less than 1 hour following coagulation activation. The plasma concentration of TAT can approach 50 ng/ml in ACS (Biasucci, L. M. et al., Circulation 93:2121-2127, 1996).

Markers Related To Myocardial Necrosis

The following are exemplary markers related to myocardial necrosis. This list is not meant to be limiting.

Cardiac Troponin

Cardiac troponin I or troponin T (cTnI and cTnT) are the preferred markers of myocardial necrosis because they allow a more sensitive detection of myocardial damage and are more specific for the myocardial tissue than the traditional "cardiac enzymes" such as creatine kinase (CK) or its isoenzyme MB (CK-MB). The troponin complex is formed by three distinct structural proteins (troponin I, C and T) and is located on the thin filament of the contractile apparatus in both skeletal and cardiac muscle tissue regulating the calcium dependent interaction of myosin and actin. The cardiac isoforms of troponin T and I are exclusively expressed in cardiac myocytes, and their detection in the blood is specific for myocardial damage [J. I. Adams, D. Abendschein and A. Jaffe, Biochemical markers of myocardial injury: is MB the choice for the 1990's?. *Circulation* 88 (1993), pp. 750-763.]. The normal plasma concentration of cTnI is <0.1 ng/ml (4 pM). After myocardial infarction, the troponin rise in peripheral blood is seen after 3-4 h with persistent elevation for up to 2 weeks. The high proportional rise of troponins, reflecting the low plasma concentrations in healthy persons, allows the detection of myocardial damage in about one-third of patients with UA even in the absence of minor CK-MB elevations [M. Galvani, F. Ottani, D. Ferrini et al., Prognostic influence of elevated values of cardiac troponin I in patients with unstable angina. *Circulation* 95 (1997), pp. 2053-2059].

Enolase (2-phospho-D glycerate hydrolyase or phosphopyruvate hydratase, EC 4.2.1.11) is a glycolytic enzyme that converts 2-phospho-D glycerate to phosphoenolpyruvate. It is a protein which is functionally active as a heterodimer assembled from a combination of three subunits: alpha, beta and gamma. The $\gamma\gamma$ and $\alpha\gamma$ isoenzymes are referred to as neuron-specific enolase (NSE) because it was initially thought that these isoenzymes were exclusively found in neurons (Rider C C & Taylor C B (1975). Evidence for a new form of enolase in rat brain. *Biochemical and Biophysical*

Research Communications, 66: 814-820.). However, it was subsequently shown that neuroendocrine cells and several non-neuronal and non-neuroendocrine cells also contained NSE. In contrast to neurons which express the γγ isoenzyme, non-neuronal cells contain predominantly the αγ isoenzyme (Marangos P J & Schmechel D E (1987). Neuron specific enolase, a clinically useful marker for neurons and neuroendocrine cells. *Annual Review of Neuroscience*, 10: 269-29). The encephalic NSE concentration ranges from 0.4 to 2.2%, and may represent up to 4% of the total soluble proteins in some neurons (Marangos P J ibid). In adult brains, higher concentrations of NSE are found in the gray matter (e.g., neocortex) and lower levels in the white matter (e.g., pyramidal tract and corpus callosum).

Besides being expressed selectively in neurons, NSE has a high stability in biological fluids and, as a free soluble cytoplasmic protein, can easily diffuse to the extracellular medium and cerebrospinal fluid (CSF) when neuronal membranes are injured. Hence, measurements of CSF-NSE (cNSE) may be an attractive marker of neuronal damage. There are some peculiarities, however, that have to be considered when cNSE or other CSF neuronal markers are assayed: nature, location and extension of the lesion; CSF turnover and time elapsed between neuronal injury and CSF sample collection.

Several studies have shown that cNSE yields a reliable estimate of the severity of neuronal injury as well as clinical outcome of patients with serious clinical manifestations such as in cases of stroke (Hay E, Royds J A, Davies-Jones G A, Lewtas N A, Timperley W R & Taylor C B (1984). Cerebrospinal fluid enolase in stroke. *Journal of Neurology, Neurosurgery and Psychiatry*, 47: 724-729.), head injury (Persson L, Hardemark H G, Gustafsson J, Rundstrom G, Mendel-Hartvig I, Esscher T & Pahlman S (1987). S-100 protein and neuron-specific enolase in cerebrospinal fluid and serum: markers of cell damage in human central nervous system. *Stroke*, 18: 911-91), anoxic encephalopathy (Roine R O, Somer H, Kaste M, Viinikka L & Karonen S L (1989). Neurological outcome after out-of-hospital cardiac arrest. Prediction by cerebrospinal fluid enzyme analysis. *Archives of Neurology*, 46: 753-756.), encephalitis (Studahl M, Rosengren L, Gunther G & Hagberg L (2000). Difference in pathogenesis between herpes simplex virus type 1 encephalitis and tick-borne encephalitis demonstrated by means of cerebrospinal fluid markers of glial and neuronal destruction. *Journal of Neurology*, 247: 636-642.), brain metastasis (Royds J A, Timperley W R & Taylor C B (1981). Levels of enolase and other enzymes in the cerebrospinal fluid as indices of pathological change. *Journal of Neurology, Neurosurgery and Psychiatry*, 44: 1129-113), and status epilepticus (Correale J, Rabinowicz A L, Heck C N, Smith T D, Loskota W J & DeGiorgio C M (1998). Status epilepticus increases CSF levels of neuron-specific enolase and alters the blood-brain barrier. *Neurology*, 50: 1388-1391.). Normal plasma concentration of the gamma gamma isoform is <10 ng/ml (120 pM).

Heart-type fatty acid binding protein (H-FABP) a 15 kD cytoplasmic protein involved in lipid homeostasis, is abundant in heart muscle, as well as the kidneys, brain, skeletal muscle and adrenals. It has recently been reported to detect early myocyte injury in patients with acute myocardial infarction (see for instance Ishii J, Wang J, Naruse H, et al. Serum concentrations of myoglobin vs human heart-type cytoplasmic fatty acid-binding protein in early detection of acute myocardial infarction. *Clin Chem* 1997; 43 :1372-8).

The use of B- and H-FABP as biomarkers for early identification and treatment stratification of MTBI patients presenting with headache, dizziness, and nausea in the emergency room may improve patient care and outcome. It is known that in patients with acute ischemic injury, rapid initiation of treatment will decrease the amount of neuronal cell death. Traumatic brain injury is a major cause of morbidity and mortality, and can give stroke-like symptoms. Although current knowledge about the pathophysiology of MTBI is limited, traumatically induced axonal damage is thought to be the pathophysiologic mechanism in MTBI (Povlishock J T, Jenkins L W. Are the pathobiological changes evoked by traumatic brain injury immediate and irreversible?. Brain Pathol 1995; 5:415-426), as demonstrated by increased concentrations of S100B and NSE. In the MTBI group of Pelsers et al, both B-FABP and H-FABP were increased in significantly (P<0.05) more cases (68% and 70%, respectively) than were S100B (45%) and NSE (51%), suggesting a difference in sensitivity. However, no significant correlations among serum concentrations of each of the biomarkers: only 45% of the samples had increases in both B-FABP and H-FABP, suggesting either different release kinetics or injury in different areas of the brain. The latter seems more likely because the release kinetics are not expected to differ among types of FABP (De Groot M J M, Wodzig K W H, Simoons M L, Glatz J F C, Hermens W T. Measurement of myocardial infarct size from plasma fatty acid-binding protein or myoglobin, using individually estimated clearance rates. Cardiovasc Res 1999; 44:315-324). The FABPs, as well as myoglobin and S100B, are cytosolic proteins and, therefore, are released simultaneously from injured cells. In addition, the release of cerebrovascular proteins into blood plasma is dependent on disruption of the blood-brain barrier [reviewed recently by Marchi et al.]. Because these proteins are of similar size (FABP, 15 kDa; myoglobin, 17 kDa; S100B, 22 kDa), they will not differentially pass through the blood-brain barrier. The similarity in the sizes of these molecules also implies that the elimination of these proteins from plasma occurs by renal clearance and at equal rates. B- and H-FABP and S100B (Jönsson H, Johnsson P, Hoglund P, Alling C, Blonquist S. Elimination of S100B and renal function after cardiac surgery. J Cardiothorac Vasc Anesth 2000; 6:698-701) have a plasma half-life of 20-25 min, indicating that the so-called diagnostic time window is limited but similar for these FABPs and S100B.

S-100 is a 21 kDa cytosolic protein that is localized in astrocytes, Schwann cells, Melanocytes, and adipocytes. It participates in cell-cell communication (astrocyte-neuron), cell growth, intracellular signal transduction, and is involved in the development and maintenance of the central nervous system. The S-100 protein family constitutes a subgroup of Ca(2+)-binding proteins of the EF-hand type comprising three dimeric isoforms, S-100a0, S-100a and S-100b, plus a number of structurally related proteins displaying 28-55% homology with S-100 subunits. Both intracellular and extracellular roles have been proposed for S-100 protein. Within cells, S-100 protein has been reported to regulate protein phosphorylation, ATPase, adenylate cyclase, and aldolase activities and Ca(2+)-induced Ca2+ release. Also, cytoskeletal systems, namely microtubules and microfilaments have been reported to be regulated by the protein in the presence of Ca2+. Some molecular targets of S-100 protein within cells, have been identified. This is the case with microtubule proteins, caldesmon, and a brain aldolase. S-100 protein has been reported to be secreted; extracellular S-100 protein can stimulate neuronal differentiation, glial proliferation, and prolactin secretion. S-100b is found mainly in glial cells and Schwann cells, where it is a major cytosolic component (Kato, K. and Kimura, S., Biochim. Biophys. Acta 842:146-150, 1985; Hasegawa, S. et al., Eur. Urol. 24:393-396, 1993). S-100 has a ±1% per year relative increase with age (C. May, J. A. Kaye, J. R. Atach, M. B. Schaprio, R. P. Friedland and S. L. Rapoport, Cerebrospinal fluid production is reduced in healthy aging. *Neurology* 40 (1990), pp. 500-503.), After either mild or severe head injury S-100B serum levels correlate both with clinical outcome at sixth month and the severity of primary and secondary brain damage [A. Raabe, C. Grolms, O. Sorge, M. Zimmermann and V. Seifert, Serum S-100B protein in severe head injury (see comments). *Neurosurgery* 45 (1999), pp. 477-483. and B. Romner, T. Ingebrigtsen, P. Kongstad and S. E. Borgesen, Traumatic brain damage: serum S-100 protein measurements related to neuroradiological findings. *J. Neurotrauma* 17 (2000), pp. 641-647.]. On the contrary, undetectable blood levels of S-100B predict normal intracranial findings on CT scan. Therefore, S-100B may be used to select patients for CT scanning after mild head injury [Romner, Ibid]. A number of authors investigated the release patterns of blood S-100B after acute stroke and demonstrated associations with the volume of lesions, clinical status and functional outcome [H. D. Abraha, R. J. Butterworth, P. W. M. Bath, W. S. Wassif, J. Garthwaite and R. A. Sherwood, Serum S-100 protein, relationship to clinical outcome in acute stroke. *Ann. Clin. Biochem.* 34 (1997), pp. 336-370; T. Büttner, S. Weyers, T. Postert, R. Sprengelmeyer and W. Khun, S-100 protein: serum marker of focal brain damage after ischemic territorial MCA infarction. *Stroke* 28 (1997), pp. 1961-1965.; K. Fassbender, R. Schmidt, A. Schreiner, M. Fatar, F. Mühlhauser, M. Daffertshofer and M. Hennerici, Leakage of brain-originated proteins in peripheral blood: temporal profile and diagnostic value in early ischemic stroke. *J. Neurol. Sci.* 148 (1997), pp. 101-105; U. Missler, M. Wiesmann, C. Friedrich and M. Kaps, S-100 protein and neuron-specific enolase concentrations in blood as indicators of infarction: volume and prognosis in acute ischemic stroke. *Stroke* 28 (1997), pp. 1956-1960.; and W. T. Wunderlich, A. B. Ebert, T. Kratz, M. Görtler, S. Jost and M. Herrmann, The early neurobehavioral outcome after stroke is related to the release of neurobiochemical markers of brain damage. *Stroke* 30 (1999), pp. 1190-1195.]. The release pattern of S-100B was interpreted to mirror the underlying pathophysiology of acute stroke. Furthermore, clinical studies demonstrated a significant association between early serum concentrations of S-100B and the clinical and/or functional outcome after stroke [Fassbender, ibid.]. Recently, Herrmann et al. [M. Herrmann, P. E. Vos, M. T. Wunderlich, C. H. de Bruijn and K. J. Lamers, Release of glial tissue-specific protein after acute stroke: a comparative analysis of serum concentrations of protein S-100B and glial fibrillary acidic protein. *Stroke* 31 (2000), pp. 2670-2677.] studied a comparative analysis of GFAP and S-100E serum concentrations in 32 patients with infarcts in the anterior circulation system after acute stroke. The release of both markers was found to be significantly correlated and the post-stroke blood values were associated with the size of brain lesions, the neurological status and the short-term outcome of the patients. However, the release pattern of both glia markers differed between different subtypes of stroke. GFAP was found to be a more sensitive marker of brain damage in patients with smaller lacunar lesions or minor strokes.

Markers Related to Coagulation

The following are exemplary markers related to coagulation. This list is not meant to be limiting.

Plasmin is the enzymatically active form of the plasminogen (Plg) zymogen. It is a 78 kDa active serine protease plasmin that crosslinks with fibrin. Plg is activated in humans by two Plg activators—tissue-type Plg activator (tPA) and urokinase-type Plg activator (uPA). Plasmin not only binds but also degrades many matrix proteins—including fibronectin, von Willebrand factor, thrombospondin, and laminin—at lysyl or arginyl peptide bonds. PAI-1 also directly inhibits plasmin (Hekman and Loskutoff 1988). PAI-1 appears to play a major role in determining the proliferative response to vascular injury by inhibiting the degradation of fibrin and several extracellular matrix proteins by plasmin. The proteolytic network of susceptible matrix proteins is further extended to include the collagens and elastin by the ability of plasmin to activate certain matrix metalloproteinases (MMPs), which, in turn, can activate still others. Also, certain growth factors, cytokines, and chemokines can be released, activated, and/or degraded by plasmin (reviewed in Carmeliet & Collen, 1997; Lijnen and Collen, 1996; Lijnen et al., 1996b; Lijnen et al., 1998; Plow et al., 1995 and Waisman, 2003). Plasmin-alpha2-antiplasmin complex (PAP) is an index of recent fibrinolytic activity. The normal serum concentration of PAP is <1 microgram/ml (6.9 nM).

Beta-thromboglobulin (betaTG) is composed of 81 amino acid residues forming into four identical subunits. It makes up 10% of the alpha granules contents, is released under the influence of known platelet activators such as ADP, collagen, immune complexes, and thrombin, and is produced by lysis of PF4 and platelet basic protein. It has a half-life in plasma of about 100 minutes. The normal plasma concentration of PTG is <40 ng/ml (1.1 nM), however, this is influenced by age, time of day, specimen anticoagulation, and certain drugs such as beta blockers. Beta TG has been shown to be significantly higher (171 IU/ml vs. 32 IU/ml, p<0.001) in stroke patients, in atherothrombotic and cardioembolic stroke, but not for lacunar infarctions (Szegedi et al. Molecular markers of endothelial dysfunction in acute ischemic stroke Ideggyogy Sz. 2002 March 20; 55(34): 102-8.).

PF4 is an abundant platelet alpha-granule constituent that is released during the process of platelet activation and that accumulates in high concentrations on endothelial cell surfaces after acute vessel injury. Human platelets contain about 20 micrograms of PF4/$10^9$ platelets, and physiologic serum concentrations are 5-10 micrograms/mL. Human PF4 is a protein of 7800 Da that contains 70 amino acid residues and exists as a tetramer at physiologic pH and tonicity. Its isoelectric point is 7.6; however, it is quite asymmetric, having an extremely anionic N-terminal domain that contains five negatively charged residues in the first seven amino acids and a cationically charged carboxy-terminal end that contains four lysine residues in the terminal 12 amino acids. Perhaps its most outstanding chemical feature is its extremely high affinity for heparin ($K_D$=5-20 nM).

Levels of PF4 in the blood may be associated with clot formation and/or any condition that causes platelet activation, such as acute stroke, atherosclerosis, or even surgery (For instance see Serebruany et al., Enhanced platelet/endothelial activation in depressed patients with acute coronary syndromes: evidence from recent clinical trials. Blood Coagul Fibrinolysis. 2003 September; 14(6):563-7; Rapold, H et al., Fibrin formation and platelet activation in patients with myocardial infarction and normal coronary arteries. Eur Heart J. 1989 April; 10(4):323-33; Nilsson J et al., Association between high levels of growth factors in plasma and progression of coronary atherosclerosis. J Intern Med. 1992 November; 232(5):397-404.).

Fibrinopeptides A and B (FPA and FPB) are released by the proteolytic action of thrombin on fibrinogen and are therefore markers of thrombin activity. FPA is a 16 amino-acid peptide cleaved from the aminoterminus of the fibrinogen-chain with a very short half-life in plasma (3-5 min). FPA that circulates in three different forms [J. A. Koehn and R. E. Canfield, Purification of human fibrinopeptides by high performance liquid chromatography. *Anal. Biochem.* 116 (1981), pp. 349-356.] is released more rapidly from fibrinogen than is FPB, resulting in the intermediate fibrin I molecule (des AA-fibrin). FPB is released from the aminoterminus of the -chain of fibrinogen or fibrin I and is a 14 amino-acid peptide. The sequential cleavage of FPA and FPB results in formation of fibrin II monomer (des AABB-fibrin).

The use of activation markers of thrombosis and fibrinolysis for early risk stratification of patients with ACS is still under study. The hypothesis currently tested is that patients who show marked elevations of these activation markers during the initial hours after symptom onset are at the highest risk of progression of coronary thrombosis and of its complications, i.e. myocardial infarction and death. Eisenberg et al. [P. R. Eisenberg, J. L. Kenzora, B. E. Sobel, P. A. Ludbrook and A. S. Jaffe, Relation between ST segment shifts during ischemia and thrombin activity in patients with unstable angina. *J. Am. Coll. Cardiol.* 18 (1991), pp. 898-903.] studied patients with unstable angina and found that those with reversible ST-segment shifts had higher FPA plasma levels than those with T-wave inversion alone. At coronary angiography, 55% of patients with ST-segment shifts had lesions with morphologic characteristics consistent with atherosclerotic plaque complicated by thrombosis compared with 22% of those with T-wave inversion. Ardissino et al [D. Ardissino, P. Merlini, G. Gamba et al., Thrombin activity and early outcome in unstable angina pectoris. *Circulation* 93 (1996), pp. 1634-1639.] have recently studied 150 patients with unstable angina and found that those with elevated FPA plasma levels had significantly higher incidence of death or non-fatal myocardial infarction than patients with normal FPA levels. These observations support the concept that the measurement in plasma of activation markers, namely FPA, may be a sensitive method to detect ongoing thrombus formation in patients with ACS. Plasma levels of FPA on admission, however, do not seem to predict clinical outcome in patients with acute myocardial infarction eligible for reperfusion, as judging from the results of a GUSTO-I substudy where patients with and without death or re-infarction at 30 days had similar FPA plasma levels at the time of hospital presentation [C. Granger, R. Becker, R. Tracy et al., Thrombin generation, inhibition and clinical outcomes in patients with acute myocardial infarction treated with thrombolytic therapy and heparin: results from the GUSTO-I Trial. GUSTO-I hemostasis substudy group. Global utilization of streptokinase and TPA for occluded coronary arteries. *J. Am. Coll. Cardiol.* 31 (1998), pp. 497-505.].

Prothrombin fragment 1+2 (F1+2) is a 32 kDa polypeptide released from the prothrombin during its activation to thrombin by the prothrombinase complex. Measurement of circulating levels of F1+2 has been considered a specific marker of thrombin generation in vivo (Bauer K A, Broekmans A W, Bertina R M, Conard J, Horellou M H, Samama M M, Rosenberg R D. Hemostatic enzyme generation in the blood of patients with hereditary protein C deficiency. *Blood.* 1988; 71: 1418-1426; Van der Poll T, Buller H R, ten Cate H, Worterl C H, Bauer K A, van Deventer S J, Hack C E, Sauwervein H P, Rosenberg R D, ten Cate J W. Activation of coagulation after administration of tumor necrosis factor to normal subjects. *N Engl J Med.* 1990; 322: 1622-1627.). Elevated F1+2 has been found in patients with peripheral arterial disease, coronary atherosclerosis, and in relation to the presence of conventional CAD risk factors, such as age, smoking, and dyslipidemia (Kienast J, Thompson S G, Raskino C, Peizer H, Fechtrup C, Osterman H, van de Loo J. Prothrombin activation fragment 1+2 and thrombin antithrombin complexes in patients with angina pectoris. Relation to the presence and severity of coronary atherosclerosis. *Thromb Haemost.* 1993; 70: 550-553; Cushman M, Psaty B M, Macy E, Bovill E G, Cornell E S, Kuller L H, Tracy R P. Correlates of thrombin markers in an elderly cohort free of clinical cardiovascular disease. *Arterioscler Thromb Vasc Biol.* 1996; 16: 1163-1169; Musial J, Pajal A, Undas A, Kavalec E, Topoi-Madry R, Pazucha T, Grzywacz M, Szczeklik A. Thrombin generation markers and coronary heart disease risk factors in a Polish population sample. *Thromb Haemost.* 1997; 77: 697-700.). F1+2 has a half-life of approximately 90 minutes in plasma.

von Willebrand factor (vWF) is a glycoprotein composed of identical disulfide-linked subunits, each comprising 2050 amino acid residues and up to 22 carbohydrate chains, for a total mass of approximately 278 kDa of which 10% 19% is carbohydrate [Titani K, Kumar S, Takio K, Ericsson L H, Wade R D, Ashida K, Walsh K A, Chopek M W, Sadler J E, Fujikawa K. Amino acid sequence of human von Willebrand factor. *Biochemistry* 1986; 25 : 3171 84.]. Two subunits joined at carboxyl terminal ends form dimers that are the building blocks of larger polymers [Mayadas T N, Wagner D D. von Willebrand factor biosynthesis and processing. *Ann N Y Acad Sci* 1991; 614: 153 66]. Inter-subunit disulfide bonds at the amino terminal ends of dimers form multimers that range in molecular mass from approximately 500 kDa to in excess of 10 000 kDa [Mayadas T N, Wagner D D. Vicinal cysteines in the prosequence play a role in von Willebrand factor multimer assembly. *Proc Natl Acad Sci USA* 1992; 89 : 3531 5]. The multimers may appear as thin filaments up to 1300 nm long, about the diameter of a platelet, or as coiled molecules with a cross-section of 200-300 nm [Fowler W E, Fretto L J. Electron microscopy of von Willebrand factor. In: Zimmerman T S, Ruggeri Z M, eds. *Coagulation and Bleeding Disorders. The Role of Factor VIII and Von Willebrand Factor.* New York: Marcel Dekker, 1989: 181 93.]. Shear forces in the circulation may 'uncoil' globular vWF molecules while they are transiently bound to vascular or cellular surfaces, but vWF bound to collagen may not undergo such a change [Novak L, Deckmyn H, Damjanovich S, Harsfalvi J. Shear-dependent morphology of von Willebrand factor bound to immobilized collagen. *Blood* 2002; 99 : 2070 6.]. There appears to be a direct correlation between the size of vWF and its ability to induce the formation of platelet thrombi. The contribution of vWF to thrombus formation is both direct, by mediating the adhesion of platelets to components of the extracellular matrix and to one another, and indirect, by associating with the procoagulant factor VIII and preventing its rapid clearance from plasma thus allowing normal thrombin generation. The main function of vWF is to mediate adhesive interactions of platelets exposed to rapid blood flow. There are two distinct platelet receptors for VWF, the glycoprotein (GP) Ibalpha in the GP Ib IX V complex and the integrin alpha.sub.IIb beta.sub.3(GP IIb IIIa complex). Platelet agglutination induced by the antibiotic ristocetin requires vWF as a cofactor and involves interaction with GP Ib alpha. The main mechanism regulating vWF size involves specific proteolysis, with a possible contribution from a disulfide bond reductase activity ascribed to thrombospondin-1. The latter process involves a rearrangement of disulfide bonds with 'depolymerization' of the larger multimers [Xie L, Chesterman C N, Hogg P J. Control of von Willebrand factor multimer size by thrombospondin-1. *J Exp Med* 2001; 193 : 1341 9.]. Thrombospondin-1 is abundant in the -granules of platelets from which it is released upon activation, and could contribute to the regulation of vWF multimer size at sites of vascular lesions, thus limiting thrombus growth.

Unlike vWF stored in cellular organelles, which contains exclusively intact subunits, plasma-derived multimers always yield upon reduction a well-defined proportion of two subunit fragments [Zimmerman T S, Dent J A, Ruggeri Z M, Nannini L H. Subunit composition of plasma von Willebrand factor. Cleavage is present in normal individuals, increased in IIA and IIB von Willebrand disease, but minimal in variants with aberrant structure of individual oligomers (Types IIC, IID and IIE). *J Clin Invest* 1986; 77 : 947 51.] that have an apparent molecular mass of 140 and 176 kDa and result from cleavage of the single bond between Tyr842 and Met843 [Dent J A, Berkowitz S D, Ware J, Kasper C K, Ruggeri Z M. Identification of a cleavage site directing the immunochemical detection of molecular abnormalities in type IIA von Willebrand factor. *Proc Natl Acad Sci USA* 1990; 87 : 6306 10.]. This event separates a multimer into two smaller species, each presenting a cleaved subunit at the amino or carboxyl terminal end. The protease that cleaves vWF at the Tyr842-Met843 bond is ADAMTS-13 ['A Disintegrin-like and Metalloprotease domain (reprolysin-type) with Thrombo spondin type I motifs'][Gerritsen H E, Robles R, Lämmle B, Furlan M. Partial amino acid sequence of purified von Willebrand factor-cleaving protease. *Blood* 2001; 98: 1654 61], and the structure of the corresponding gene has been fully characterized [Zheng X, Chung D, Takayama T K, Majerus E M, Sadler J E, Fujikawa K. Structure of von Willebrand factor-cleaving protease (ADAMTS13), a metalloprotease involved in thrombotic thrombocytopenic purpura. *J Biol Chem* 2001; 276 : 41059 63]. The regulation of plasma vWF multimer size is an important process that may influence the onset and progression of arterial thrombosis, possibly with a pathogenic role in common conditions such as the acute occlusive complications of coronary artery disease. Elevated vWF has been shown to be a result of stroke and stroke subtype (Catto A J, Carter A M, Barrett J H, Bamford J, Rice P J, Grant P J. von Willebrand factor and factor VIII: C in acute cerebrovascular disease. Relationship to stroke subtype and mortality; Qizilbash N, Duffy S, Prentice C R, Boothby M, Warlow C. Von Willebrand factor and risk of ischemic stroke. Neurology. 1997 December; 49(6):1552-6.).

Tissue factor (TF) is a cell membrane-bound glycoprotein (MW 46 kDa) and a member of the class 2 cytokine receptor family. It is composed of a hydrophilic extracellular domain, a membrane-spanning hydrophobic domain, and a cytoplasmic tail of 21 residues, including a non-disulfide-linked cysteine. The mature protein, which is post-translationally modified to include carbohydrate moieties, is biologically active. Upon exposure to blood, perivascular cell-bound TF binds to factor VII, a vitamin K-dependent serine protease unique among coagulation factor zymogens in that it exists in a partially active state. Cleavage of factor VII to VIIa by thrombin, factor IXa, Xa, or XIIa increases its activity 100-fold. The affinity of TF for factor VIIa is increased by anionic phospholipids. The TF-factor VIIa complex can directly or indirectly activate factor X and thence generate thrombin (factor IIa). TF mediates hemostasis by: 1) complexing with factor VIIa to directly convert X to Xa (extrinsic pathway); or 2) indirectly generating Xa by converting IX to IXa, which, in turn, complexes with VIIIa to convert X to Xa (intrinsic pathway). Factor Xa, once generated, complexes with its co-factor, Va, to convert prothrombin (II) to thrombin (IIa) which, in turn, cleaves fibrinogen to generate fibrin or activate platelets. Among the inhibitors of these processes are TF pathway inhibitor (TFPI), and activated Protein C complexed with Protein S (APC/S). Heparin co-factor II, antithrombin III (ATIII), and alpha-2-macro-globulin are potent anti-thrombin agents which form ternary complexes with vitronectin (Vn) and heparin. Fibrinolysis is mediated by tissue-type type plasminogen activator (tPA), and inhibited by PAI-1, bound to Vn. The latter also exerts anti-thrombin effects. Under physiological conditions TF is expressed by cells not in contact with blood such as vascular smooth muscle, mesenchymal and epithelial cells including placental villous stromal cells. However, TF is not normally expressed by cells in contact with the circulation (i.e., endothelium and villous trophoblasts). The pathological induction of TF expression in the endothelium contributes to the intravascular thrombosis of atherosclerosis and septic shock. Due to their perivascular location, enhanced TF expression by human endometrial DCs provides a mechanism to prevent hemorrhage during trophoblast invasion of the endometrial vasculature. Tissue factor expression is controlled at the transcriptional level in various cell types. Cytokines, growth factors, and serum transiently (1-4 hours) induce TF mRNA and protein in cultured cells from diverse tissues. The normal serum concentration of TF is <0.2 ng/ml (4.5 pM). In addition to hemostasis, TF is now known to mediate invasion and angiogenesis. These functions apparently require interaction with factor VIIa. Tissue factor has been shown to be correlated with both stroke (Abumiya T, Yamaguchi T, Terasaki T, Kokawa T, Kario K, Kato H. Decreased plasma tissue factor pathway inhibitor activity in ischemic stroke patients. Thromb Haemost. 1995 October; 74(4):1050-) and stroke subtype (Hirashima Y, Nakamura S, Suzuki M, Kurimoto M, Endo S, Ogawa A, Takaku A. Cerebrospinal fluid tissue factor and thrombin-antithrombin III complex as indicators of tissue injury after subarachnoid hemorrhage. Stroke. 1997 September; 28(9):1666-70.), and Atherosclerosis (Tremoli E, Camera M, Toschi V, Colli S. Tissue factor in atherosclerosis. Atherosclerosis. 1999 June; 144(2):273-83.).

Markers Related to Atherosclerotic Plaque Rupture

The following are exemplary markers related to Atherosclerotic Plaque Rupture. This list is not meant to be limiting.

Atherosclerotic plaque rupture is part of a dynamic inflammatory process of atherosclerotic vascular disease which starts from inception and continues through plaque growth, rupture and ultimately thrombosis. Suggested markers of atherosclerotic plaque rupture that would be suitable for inclusion in a stroke or stroke sub-type diagnostic include human neutrophil elastase, inducible nitric oxide synthase, lysophosphatidic acid, malondialdehyde-modified low density lipoprotein, and various members of the matrix metalloproteinase (MMP) family, including MMP-1, -2, -3, 7, 9, 12, and -19, the main family members of which we discuss below.

Matrix metalloproteinases (MMPs) are a family of zinc-binding proteolytic enzymes that normally remodel the extracellular matrix and pathologically attack substrates as part of the neuroinflammatory response. MMP-2 (72 kDa, gelatinase A) and MMP-9 (92 kDa, gelatinase B) specifically attack type IV collagen, laminin, and fibronectin, which are the major components of the basal lamina around cerebral blood vessels. Proenzyme activation and enzyme activities are tightly regulated by tissue inhibitors of MMPs (TIMPs) and interactions with surrounding extracellular matrix molecules. Matrix metalloproteinases (MMPs) and tissue inhibitors of metalloproteinases (TIMPs) play a significant role in regulating angiogenesis, the process of new blood vessel formation. Interstitial collagenase (MMP-1), 72 kDa gelatinase A/type IV collagenase (MMP-2), and 92 kDa gelatinase B/type IV collagenase (MMP-9) dissolve extracellular matrix (ECM) and may initiate and promote angiogenesis. TIMP-1, TIMP-2, TIMP-3, and possibly, TIMP-4 inhibit neovascularization. A new paradigm is emerging that matrilysin (MMP-7), MMP-9, and metalloelastase (MMP-12) may block angiogenesis by converting plasminogen to angiostatin, which is one of the most potent angiogenesis antagonists. MMPs and TIMPs play a complex role in regulating angiogenesis. MMP-9 has been implicated as a marker of stoke severity (Montaner et al., Matrix Metalloproteinase Expression After Human Cardioembolic Stroke, *Stroke*. 2001; 32:1759.)

Markers Related to Tissue Injury and Inflammation

The following are exemplary markers related to inflammation. This list is not meant to be limiting.

C-reactive protein (CRP) is composed of 5 23-kd subunits. CRP is a member of the pentraxin family of innate immune response proteins. Although initially believed to be synthesized only by the liver in response to interleukin-6, recent evidence indicates that CRP is also produced in smooth muscle cells within human coronary arteries and is expressed preferentially in diseased vessels. [P. Calabro, J. T. Willerson and E. T. Yeh, Inflammatory cytokines stimulated C-reactive protein production by human coronary artery smooth muscle cells, *Circulation* 108 (2003), pp. 1930-1932.] and [W. J. Jabs, E. Theissing and M Nitschke et al., Local generation of C-reactive protein in diseased coronary artery venous bypass grafts and normal vascular tissue, *Circulation* 108 (2003), pp. 1428-1431.] One report found that levels of CRP mRNA within atherosclerotic plaque were 7- and 10-fold higher than levels found in the liver and normal blood vessels, respectively [K. Yasojima, C. Schwab, E. G. McGeer and P. L. McGeer, Generation of C-reactive protein and complement components in atherosclerotic plaques, *Am J Pathol* 158 (2001), pp. 1039-1051.]. Although traditionally considered a passive downstream marker of the inflammatory process, CRP has been shown in laboratory studies to influence vascular vulnerability directly by a variety of mechanisms, including enhanced expression of local endothelial cell surface adhesion molecules, monocyte chemoattractant protein-1, [V. Pasceri, J. T. Willerson and E. T. Yeh, Direct proinflammatory effect of C-reactive protein on human endothelial cells, *Circulation* 102 (2000), pp. 2165-2168.] and [V. Pasceri, J. S. Cheng, J. T. Willerson, E. T. Yeh and J. Chang, Modulation of C-reactive protein-mediated monocyte chemoattractant protein-1 induction in human endothelial cells by anti-atherosclerosis drugs, *Circulation* 103 (2001), pp. 2531-2534.] endothelin-1, and endothelial plasminogen activator inhibitor-1; reduced endothelial nitric oxide bioactivity; [S. Verma, S. H. Li and M. V Badiwala et al., Endothelin antagonism and interleukin-6 inhibition attenuate the proatherogenic effects of C-reactive protein, *Circulation* 105 (2002), pp. 1890-1896][S. K. Venugopal, S. Devaraj, I. Yuhanna, P. Shaul and I. Jialal, Demonstration that C-reactive protein decreases eNOS expression and bioactivity in human aortic endothelial cells, *Circulation* 106 (2002), pp. 1439-1441.] and [S. Verma, C. H. Wang and S. H Li et al., A self-fulfilling prophecy C-reactive protein attenuates nitric oxide production and inhibits angiogenesis, *Circulation* 106 (2002), pp. 913-919.] increased induction of tissue factor in monocytes; increased LDL uptake by macrophages; [T. P. Zwaka, V. Hombach and J. Torzewski, C-reactive protein-mediated low density lipoprotein uptake by macrophages Implications for atherosclerosis, *Circulation* 103 (2001), pp. 1194-1197.] and colocalization with the complement membrane attack complex within atherosclerotic lesions. Recent data also indicate that the expression of human CRP in CRP-transgenic mice directly enhances intravascular thrombosis in arterial injury and photochemical injury models of endothelial disruption [H. D. Danenberg, A. J. Szalai and R. V Swaminathan et al., Increased thrombosis after arterial injury in human C-reactive protein-transgenic mice, *Circulation* 108 (2003), pp. 512-515.]. The normal plasma concentration of CRP is <3 micrograms/ml (30 nM) in 90% of the healthy population, and <10 micrograms/ml (100 nM) in 99% of healthy individuals. Elevated levels of CRP have been shown to predict stroke risk (Gussekloo et al., C-reactive protein is a strong but nonspecific risk factor of fatal stroke in elderly persons. Arterioscler Thromb Vasc Biol. 2000 April; 20(4): 1047-51.) and occurance (Ford E S, Giles W H. Serum C-reactive protein and self-reported stroke: findings from the Third National Health and Nutrition Examination Survey. Arterioscler Thromb Vasc Biol. 2000 April; 20(4):1052-6.).

IL-1 ligands (IL-1 and IL-1 beta, collectively referred to as IL-1) are pluripotent, proinflammatory cytokines that orchestrate inflammatory and host defense responses in the body. IL-1 augments T-cell responses to mitogens (and indirectly activates B cells), increases expression of vascular adhesion molecules, and induces a number of other proinflammatory cytokines, chemokines, and inflammation-associated molecules that form an amplifying cascade to stimulate an immune response. The net effect of inducing these other immune stimulatory molecules is to recruit and activate macrophages, lymphocytes, and neutrophils to fight infection and to stimulate wound healing in response to tissue damage (Dinarello, [1996]).

All ligands and receptor components of the IL-1 family (IL-1, IL-1, IL-1ra, IL-1R1, IL-1RII, AcP) are present within the brain, although they are expressed at low levels in the healthy central nervous system (CNS) (Vitkovic et al., [2000]). Microglia express caspase 1, the enzyme responsible for cleaving pro-IL-1 to its active form, and seem to be the earliest and major source of IL-1 after experimental CNS injury, infection, or inflammation (Eriksson et al., [1999]). Neurons, astrocytes, oligodendrocytes, and endothelial cells may also produce IL-1, but evidence suggests that their production is subsequent to the microglial response (Blasi et al., [1999]; Davies et al., [1999]; Pearson et al., [1999]; Vitkovic et al., [2000]). Several interleukins have been implicated as diagnostic markers of stroke, including IL-1 (Vila N, Chamorro A. Cytokines and acute-phase response in acute stroke. Stroke. 1995 September; 26(9):1729.) IL-6 (Tarkowski et al., Early intrathecal production of interleukin-6 predicts the size of brain lesion in stroke. Stroke. 1995 August; 26(8):1393-8; Kim J S. Cytokines and adhesion molecules in stroke and related diseases. J Neurol Sci. 1996 May; 137(2):69-78) IL-1 beta, II-8, and IL-17 (Kostulas N et al., Increased IL-1beta, IL-8, and IL-17 mRNA expression in blood mononuclear cells observed in a prospective ischemic stroke study. Stroke. 1999 October; 30(10):2174-9.) and IL-1 receptor agonist (Basu A et al., The type 1 interleukin-1 receptor is essential for the efficient activation of microglia and the induction of multiple proinflammatory mediators in response to brain injury. J. Neurosci. 2002 July 15; 22(14): 6071-82.).

The family of IL (interleukin)-6-type cytokines comprises IL-6, IL-11, LIF (leukaemia inhibitory factor), OSM (oncostatin M), CNTF (ciliary neurotrophic factor), CT-1 (cardiotrophin-1) and CLC (cardiotrophin-like cytokine). They activate target genes involved in differentiation, survival, apoptosis and proliferation. The members of this cytokine family have pro- as well as anti-inflammatory properties and are major players in haematopoiesis, as well as in acute-phase and immune responses of the organism. IL-6-type cytokines bind to plasma membrane receptor complexes containing the common signal transducing receptor chain gp 130 (glycoprotein 130). Signal transduction involves the activation of JAK (Janus kinase) tyrosine kinase family members, leading to the activation of transcription factors of the STAT (signal transducers and activators of transcription) family. Another major signalling pathway for IL-6-type cytokines is the MAPK (mitogen-activated protein kinase) cascade. Receptors involved in recognition of the IL-6-type cytokines can be subdivided in the non-signalling α-receptors (IL-6R α, IL-11R α, and CNTFR α, where R refers to receptor) and the signal transducing receptors (gp130, LIFR, and OSMR). The latter associate with JAKs and become tyrosine phosphorylated in response to cytokine stimulation. Each of the IL-6-type cytokines is characterized by a certain profile of receptor recruitment that in all cases involves at least one molecule of gp130. IL-6, IL-11 and CNTF first bind specifically to their respective □-receptor subunits. Here, only the complex of cytokine and α-receptor efficiently recruits the signalling receptor subunits. Also, an α-receptor subunit has been postulated for CT-1 [Robledo, O., Fourcin, M., Chevalier, S., Guillet, C., Auguste, P., Pouplard-Barthelaix, A., Pennica, D. and Gascan, H. (1997) Signaling of the cardiotrophin-1 receptor. Evidence for a third receptor component. J. Biol. Chem. 272, 4855-4863], but since this putative receptor protein has not been cloned yet its existence is questionable. IL-6 and IL-11 are the only IL-6-type cytokines that signal via gp130 homodimers. The remaining IL-6 type cytokines signal via heterodimers of either gp130 and the LIFR (LIF, CNTF, CT-1 and CLC) or gp130 and the OSMR (OSM). Human OSM has the exceptional capability to recruit two different receptor complexes. It forms both LIFR-gp130 and OSMR-gp130 heterodimers. LIF and OSM directly engage their signalling receptor subunits without requirement for additional α-receptor subunits.

The normal serum concentration of IL-6 is <3 pg/ml (0.15 pM). Interleukin-6 has been emphasized by reports of elevated circulating as well as intracardiac IL-6 levels in patients with congestive heart failure (MacGowan G A, Mann D L, Kormos R L, et al. Circulating interleukin-6 in severe heart failure. Am J Cardiol 1997; 79: 1128-31.). In addition, IL-6 has been diagnostic of stroke (Kim J S et al., Serial measurement of interleukin-6, transforming growth factor-beta, and S-100 protein in patients with acute stroke. Stroke. 1996 September; 27(9):1553-7.).

Tumor necrosis factor alpha (TNF-α) is a protein of 185 amino acids glycosylated at positions 73 and 172. It is synthesized as a precursor protein of 212 amino acids. Monocytes express at least five different molecular forms of TNF-alpha with molecular masses of 21.5-28 kDa. They mainly differ by post-translational alterations such as glycosylation and phosphorylation. TNF-alpha is produced by many different cell types. The main sources in vivo are stimulated monocytes, fibroblasts, and endothelial cells. Macrophages, T-cells and B-lymphocytes, granulocytes, smooth muscle cells, eosinophils, chondrocytes, osteoblasts, mast cells, glial cells, and keratinocytes also produce TNF-alpha after stimulation. Glioblastoma cells constitutively produce TNF-alpha and the factor can be detected also in the cerebrospinal fluid. Human milk also contains TNF-alpha. The normal serum concentration of TNF-alpha is <40 pg/ml (2 pM). Elevations in the plasma concentration of TNF-alpha are associated with any proinflammatory condition, including trauma, stroke, and infection. TNF.alpha. has a half-life of approximately 1 hour in the bloodstream, indicating that it may be removed from the circulation soon after symptom onset. A rapid overproduction of TNF-alpha in a cerebral post-ischemic inflammatory response leads to the stimulation of adhesive molecules expression with subsequent accumulation of leukocytes in the ischemic focus, which is preceded by their adhesion and migration. The TNF-alpha proinflammatory activity results mainly in extending the area of the brain infarct, which brings about negative clinical implications. Being the final morphological effect of ischemic stroke, TNF-alpha appears also to contribute to neuronal necrosis by its involvement in the process of apoptosis as well as in the death of neurons.

Intercellular adhesion molecule (sICAM-1), also called CD54, is an 85-110 kDa Ig-like cell adhesion molecule expressed by several cell types, including leukocytes and endothelial cells. It can be induced in a cell-specific manner by several cytokines, for example, tumor necrosis factor-alpha, interleukin-1, and interferon-gamma, and inhibited by glucocorticoids. The normal plasma concentration of ICAM-1 is approximately 250 ng/ml (2.9 nM). ICAM-1 plays a role in inflammatory processes and in the T-cell mediated host defense system. It functions as a costimulatory molecule on antigen-presenting cells to activate MHC class II restricted T-cells, and on other cell types in association with MHC class I to activate cytotoxic T-cells. ICAM-1 on endothelium plays an important role in migration of (activated) leukocytes to sites of inflammation. ICAM-1 is shed by the cell and detected in plasma as sICAM-1. Derangement of ICAM-1 expression probably contributes to the clinical manifestations of a variety of diseases, predominantly by interfering with normal immune function. Among these are malignancies (e.g., melanoma and lymphomas), many inflammatory disorders (e.g., asthma and autoimmune disorders), atherosclerosis, ischemia, certain neurological disorders, and allogeneic organ transplantation (O'Malley T, Ludlam C A, Riemermsa R A, Fox K A. Early increase in levels of soluble inter-cellular adhesion molecule-1 (sICAM-1); potential risk factor for the acute coronary syndromes. Eur Heart J. 2001 July; 22(14):1226-34.).

VCAM-1 (vascular cell adhesion molecule-1), or CD106, contains six or seven immunoglobulin domains and is expressed on both large and small vessels only after the endothelial cells are stimulated by cytokines. The sustained expression of VCAM-1 lasts over 24 hours. Primarily, VCAM-1 is an endothelial ligand for VLA-4 (Very Late Antigen-1 or alpha4beta1) of the beta 1 subfamily of integrins and for integrin alpha4beta7. VCAM-1 promotes the adhesion of lymphocytes, monocytes, eosinophils, and basophils. Interestingly, certain melanoma cells can use VCAM-1 to adhere to the endothelium, and VCAM-1 may participate in monocyte recruitment to atherosclerotic sites. The normal serum concentration of sVCAM is approximately 650 ng/ml (6.5 nM). VCAM levels are elevated in MI and with unstable angina. Endothelial VCAM of inflammatory response appear within hours of the initial ACS event and remainelevated for up to 6 months at levels that may reflect the progression of the inflammatory process. Increased level of VCAM, drawn during presentation of ACS, was a significant predictor of recurrent ischemia, nonfatal MI, and cardiac death 6 months after the initial event (P<0.001) (Mulvihill N, Foley J B, Murphy R T, Curtin R, Crean P A, Walsh M. 2001. Risk stratification in unstable angina and non-Q wave myocardial infarction using soluble cell adhesion molecules. Heart 85(6):623-7.). Mulvihill reported that although both VCAM and C-reactive protein were elevated in patients with adverse outcomes, VCAM had a higher specificity than C-reactive protein (69% versus 52%, respectively).

Human macrophage chemoattractant protein-1 (MCP-1) also called human macrophage/monocyte chemotactic and activating factor (MCAF). MCP-1 is an 8.5 kDa protein containing 76 amino acid residues. It plays an important role in the inflammatory response of blood monocytes and tissue macrophages. Studies have revealed that MCAF/MCP-1 has in vitro multiple functions against monocytes/macrophages. MCAF/MCP-1 induces intracellular calcium influx, respiratory burst, expression of adhesion molecules such as Beta 2 integrins, and release of lysosomal enzymes in monocytes as IL-8 does against neutrophils. Moreover, MCAF/MCP-1 induces monocytes to produce tissue factor and pro-inflammatory cytokines such as IL-1 and IL-6, and enhances the tumoricidal activity of monocytes against several types of cancer cells. In addition to these effects on monocytes/macrophages, MCAF/MCP-1 induces chemotaxis, release of histamine and leukotriene, and intracellular calcium influx in basophils. Moreover, MCAF/MCP-1 chemoattracts both CD4+ and CD8+ T lymphocytes and augments the avidity of VLA-4 and VLA-5 on T lymphocytes. In addition to MCP-1, several other CC chemokines have been found to be associated with advanced atherosclerotic lesions: MIP-1alpha and MIP-1beta are expressed by T-cells in human plaques [J. N. Wilcox, N. A. Nelken, S. R. Coughlin, D. Gordon and T. J. Schall, Local expression of inflammatory cytokines in human atherosclerotic plaques. *J. Atheroscler. Thromb.* 1 Suppl 1 (1994), pp. S3-S10.] and the number of T-cells expressing these chemokines correlates with the total number of T-cells found in the plaques. RANTES is also expressed by lesion T-cells but in a smaller population (about 5%). MCP-4 is expressed in advanced plaques by endothelial cells of the vasa vasorum and in lesional macrophages [J. M. Paftison, P. J. Nelson, P. Huie, R. K. Sibley and A. M. Krensky, RANTES chemokine expression in transplant-associated accelerated atherosclerosis. *J. Heart Lung Transplant* 15 (1996), pp. 1194-1199.]. It has also been recently found that two lymphocyte specific chemoattractants, PARC/DC-CK1 and ELC, are highly expressed in human atherosclerotic plaques, PARC exclusively by macrophages and ELC by macrophages and SMC [T. J. Reape, K. Rayner, C. D. Manning, A. N. Gee, M. S. Barnette, K. G. Burnand and P. H. E. Groot, Expression and cellular localisation of the CC chemokines PARC and ELC in human atheroscerotic plaques. *Am. J. Pathol.* 154 (1999), pp. 365-374.]. In contrast to its expression pattern in atherosclerotic plaques, RANTES is highly expressed in human transplant-associated accelerated atherosclerosis by macrophages, lymphocytes, myofibroblasts and endothelial cells. MCP-1 levels have been seen to be elevated in stroke (Kim J S. Cytokines and adhesion molecules in stroke and related diseases. J Neurol Sci. 1996 May; 137(2):69-78).

IL-10 is an 18.7-kd protein expressed by a variety of human immune cells, including both T H1 and T H2 cells, B cells, monocytes-macrophages, dendritic cells, mast cells, and eosinophils. In mouse models IL-10 has been associated with inflammatory arthritis, [E. Quattrocchi, M. J. Dallman, A. P. Dhillon, A. Quaglia, G. Bagnato and M. Feldmann, Murine IL-10 gene transfer inhibits established collagen-induced arthritis and reduces adenovirus-mediated inflammatory responses in mouse liver. *J Immunol* 166 (2001), pp. 5970-5978.] and allergic inflammation. [K. G. Tournoy, J. C. Kips and R. A. Pauwels, Endogenous interleukin-10 suppresses allergen-induced airway inflammation and nonspecific airway responsiveness. *Clin Exp Allergy* 30 (2000), pp. 775-783] IL-10 has a number of documented antiallergic properties that might be important to immunotherapy (I. Bellinghausen, J. Knop and J. Saloga, The role of interleukin 10 in the regulation of allergic immune responses. *Int Arch Allergy Immunol* 126 (2001), pp. 97-101). These include inhibition of human eosinophil cytokine production and survival. [S. Takanaski, R. Nonaka, Z. Xing, P. O'Byrne, J. Dolovich and M. Jordana, Interleukin 10 inhibits lipopolysaccharide-induced survival and cytokine production by human peripheral blood eosinophils. *J Exp Med* 180 (1994), pp. 711-715.]. II-10 has been shown to be associated with the early clinical course of patients with acute ischemic stroke, especially in patients with small vessel disease or subcortical infarctions (Vila N, Castillo J, Davalos A, Esteve A, Planas A M, Chamorro A Levels of anti-inflammatory cytokines and neurological worsening in acute ischemic stroke. Stroke. 2003 March; 34(3):671-5), with hemhorrage (Dziedzic T, Bartus S, Klimkowicz A, Motyl M, Slowik A, Szczudlik A. Intracerebral hemorrhage triggers interleukin-6 and interleukin-10 release in blood. Stroke. 2002 September; 33(9):2334-5.) and stroke (Tarkowski A. Intrathecal release of pro- and anti-inflammatory cytokines during stroke. Clin Exp Immunol. 1997 December; 110(3):492-9.).

Markers Specifically Related to Neural Tissue Injury

The following are exemplary markers related to neural tissue injury. This list is not meant to be limiting.

Neurotrophins are a family of growth factors expressed in the mammalian nervous system. Some examples of neurotrophins include nerve growth factor (NGF), brain-derived neurotrophic factor (BDNF), ciliary neurotrophic factor (CNTF), basic fibroblast growth factor (bFGF) and glial derived neurotrophic factor (GDNF), neurotrophin-4/5 (NT-4/5), NT-6, and neurotrophin-3 (NT-3). These neurotrophins have also been found to be expressed in a variety of non-neuronal tissues such as cardiovascular, immune, endocrine and reproductive systems.

Glial fibrillary acidic protein (GFAP) is the major intermediate filament protein of the astrocyte, and body fluid levels of GFAP are an important tool for estimating astrogliosis and astrocytic activation in vivo. GFAP is coded on chromosome 17q21.1-q25 and consists of 432 amino acids (Reeves et al., 1989). The corresponding molecular mass is 49.8 kDa. Cytoskeletal GFAP is tightly packed into polymers. After break-up of the GFAP polymer, a soluble fragment of GFAP of approximately 41 kDa is released into the adjacent fluid compartments (Eng and Ghirnikar, 1994). Elevations of GFAP in serum can be attributed to neural tissue injury due to ischemia, coupled with increased permeability of the blood brain barrier. GFAP has been shown to be elevated in the CSF (Aurell A. et al., Determination of S-100 and glial fibrillary acidic protein concentrations in cerebrospinal fluid after brain infarction. Stroke. 1991 October; 22(10):1254-8) and serum (Niebroj-Dobosz I. et al., Immunochemical analysis of some proteins in cerebrospinal fluid and serum of patients with ischemic strokes. Folia Neuropathol. 1994; 32(3):129-37. Release of glial tissue-specific proteins after acute stroke: A comparative analysis of serum concentrations of protein S-100B and glial fibrillary acidic protein. Stroke. 2000 November; 31(11):2670-7.) of patients with stroke and stroke subtype (Runnerstam M et al., Extracellular glial fibrillary acidic protein and amino acids in brain regions of patients with subarachnoid hemorrhage—correlation with level of consciousness and site of bleeding. Neurol Res. 1997 August; 19(4):361-8.).

Myelin basic protein (MBP) is one of two major protein components of CNS myelin. MBP usually refers to the 'classic' 18.5 kDa isoform, which is one of the most abundant proteins of the myelin sheath of the adult human and bovine CNS. However, the 18.5 kDa MBP isoform is only part of a family of developmentally expressed, translocatable, and highly post-translationally modified proteins, with a multiplicity of binding partners. Since 18.5 kDa MBP's primary role has long been accepted to be stabilising the myelin sheath. Myelin formation and maintenance requires complex interactions between neurons and glia, and between the integral protein and lipid components of the myelin sheath. The normal serum concentration of MBP is <7 ng/ml (400 pM). Serum MBP is elevated after all types of severe stroke, and is correlated with the level of damage (Cerebrospinal fluid membrane-bound tissue factor and myelin basic protein in the course of vasospasm after subarachnoid hemorrhage. Hirashima Y et al., Neurol Res. 2001 October; 23(7):715-20.), while elevations in MBP concentration are not reported in the serum of individuals with strokes of minor to moderate severity, which would include lacunar infarcts or transient ischemic attacks (Palfreyman, J. W. et al., Clin. Chim. Acta 92:403-409, 1979). Normal levels of MBP in serum have an upper limit of 7 ng/ml (400 pM), but depending upon the severity of damage, exceed 120 ng/ml (6.9 nM). Due to the correlation between severity of damage and the release of MBP (Strand T. et al., Brain and plasma proteins in spinal fluid as markers for brain damage and severity of stroke. Stroke. 1984 January-February; 15(1):138-44.), stroke severity will affect the release kinetics by changing the length of time that MBP is elevated in the serum. Serum MBP elevates on the order or 1-3 hours after stroke onset, plateauing its concentration 2-5 days following stroke onset, and then decreases to normal levels over 7-9 days.

Neural cell adhesion molecule (NCAM), also called CD56, is a 170 kDa member of a family of cell surface sialoglycoproteins mediating homotypic and heterotypic cell-cell interactions. Neural cell adhesion molecules NCAM and L1 to regulate axon growth, guidance, and synaptic plasticity. Recent research findings suggest (Panicker et al., Cellular signalling mechanisms of neural cell adhesion molecules. Front Biosci. 2003 May 1; 8:d900-11.) that these molecules signal in part through integrins leading to cytoskeletal rearrangements locally in the growth cone or cell leading edge, and are expressed on the surface of astrocytes, oligodendrocytes, Schwann cells, neurons, and axons. Normal serum concentration of NCAM is <20 units/ml. NCAM has been reported as a marker for hypoxic-ischemic damage (Karkela J, et al., CSF and serum brain-specific creatine kinase isoenzyme (CK-BB), neuron-specific enolase (NSE) and neural cell adhesion molecule (NCAM) as prognostic markers for hypoxic brain injury after cardiac arrest in man. J Neurol Sci. 1993 May; 116(1):100-9.).

Neuron specific enolase (NSE) is the gamma gamma isoform of the five isozymes of the glycolytic enzyme, enolase. This enzyme is released into the CSF when neural tissue is injured. Neoplasms derived from neural or neuroendocrine tissue may release NSE into the blood. The normal serum concentration of NSE is <12.5 ng/ml (160 pM). Serum NSE has a half-life of approximately 20 hours. NSE has been reported to be elevated in the blood from patients suffering from ischemic stroke (Fassbender et al., Leakage of brain-originated proteins in peripheral blood: temporal profile and diagnostic value in early ischemic stroke. J Neurol Sci. 1997 May 1; 148(1):101-5.), infarction volume and prognosis (Missler U et al., S-100 protein and neuron-specific enolase concentrations in blood as indicators of infarction volume and prognosis in acute ischemic stroke. Stroke. 1997 October; 28(10):1956-60), and neural damage (Cunningham et al., Serum neurone specific enolase (NSE) levels as an indicator of neuronal damage in patients with cerebral infarction. Eur J Clin Invest. 1991 October; 21 (5):497-500.). Serum NSE is elevated after 4 hours from stroke onset, with concentrations reaching a maximum 1-3 days after onset. After the serum concentration reaches its maximum, which can exceed 300 ng/ml (3.9 nM), levels of serum NSE gradually decrease to normal concentrations over approximately one week. Like MBP, NSE will be present in the serum for a longer period of time as the severity of injury increases.

Additional Markers that are Non-Specific for Cellular Injury. This list is not meant to be limiting.

Human vascular endothelial growth factor (VEGF) is a key player of angiogenesis in health and disease. VEGF binds the receptor tyrosine kinases VEGFR-1 (Flt-1) and VEGFR-2 (KDR/Flk-1). Numerous studies indicate that VEGFR-2 transmits critical angiogenic signals in response to VEGF (Ferrara N. 2001. Role of vascular endothelial growth factor in regulation of physiological angiogenesis. Am J Physiol Cell Physiol 280:C1358-1366.). Alternative splicing of the VEGF gene gives rise to several VEGF isoforms with molecular masses of 121, 145, 165 or 189 kDa. Translation of these VEGF isoforms is initiated at a classical AUG start codon. Translation initiation at an additional CUG codon, in frame with the AUG start codon, generates a much larger VEGF form (L-VEGF). As proteolytic processing of L-VEGF generates a C-terminal fragment, identical to the secreted AUG-initiated isoforms, L-VEGF might constitute an intracellular store of VEGF. Neuropilin-1 (NP-1) is a specific receptor for the VEGF165 isoform and a co-receptor of VEGFR-2. (Soker S, Takashima S, Miao H Q, Neufeld G, Klagsbrun M. 1998. Neuropilin-1 is expressed by endothelial and tumor cells as an isoformspecific receptor for vascular endothelial growth factor. Cell 92:735-745.) NP-1 also binds semaphorin3A (Sema3A), a neurorepellant implicated in guidance of axons. Neuropilin-2 (NP-2) binds VEGF165 and VEGF145, as well as Sema3C and Sema3F. The fact that NP-1 and NP-2 bind semaphorins and VEGF suggests that these receptors have roles in both the nervous and cardiovascular system. The expression of VEGF predict the onset of cerebral vasospasm after aneurysmal subarachnoid hemorrhage (McGirt et al. Serum von Willebrand factor, matrix metalloproteinase-9, and vascular endothelial growth factor levels predict the onset of cerebral vasospasm after aneurysmal subarachnoid hemorrhage. Neurosurgery. 2002 November; 51(5):1128-34; discussion 1134-5.), acute ischemic stroke (Slevin M et al., Activation of MAP kinase (ERK-1/ERK-2), tyrosine kinase and VEGF in the human brain following acute ischaemic stroke. Neuroreport. 2000 August 21; 11(12):2759-64.) and hemorrhage (Cheng S Y et al., Intracerebral tumor-associated hemorrhage caused by overexpression of the vascular endothelial growth factor isoforms VEGF121 and VEGF165 but not VEGF189. Proc Natl Acad Sci USA. 1997 October 28; 94(22):12081-7.). [0171] Adhesion molecules are involved in the inflammatory response to injury. Examples of such adhesion molecules include E-selectin, intercellular adhesion molecule-1, vascular cell adhesion molecule, and other similar molecules.

E-selectin, also called ELAM-1 and CD62E, is a 140 kDa cell surface C-type lectin expressed on inflamed endothelial cells in response to treatment with inflammatory cytokines Bevilacqua et al., 1989). Intravital microscopic experiments have shown that its function in mediating leukocyte rolling is largely redundant with that of P-selectin (Hickey et al., 1999; Bullard et al., 1996; Kunkel and Ley, 1996). Some reports show elevated E-selectin levels following stroke (Stanimirovic D et al., Increase in surface expression of ICAM-1, VCAM-1 and E-selectin in human cerebromicrovascular endothelial cells subjected to ischemia-like insults. Acta Neurochir Suppl. 1997; 70:12-6.) while others show no difference (Shyu K G, Chang H, Lin C C. Serum levels of intercellular adhesion molecule-1 and E-selectin in patients with acute ischaemic stroke. J Neurol. 1997 February; 244(2):90-3.).

[0174] Markers Specifically Related to Apoptosis

Apoptosis is one of the main types of programmed cell death (PCD). As such, it is a process of deliberate suicide by an unwanted cell in a multicellular organism. In contrast to necrosis, which is a form of cell death that results from acute tissue injury, apoptosis is carried out in an ordered process that generally confers advantages during an organism's life cycle. We now introduce several markers related to apoptosis, however, this list is not meant to be limiting.

Caspases are a family of cysteine proteases that cleave proteins after aspartic acid residues. They are the main effectors of apoptosis or programmed cell death (PCD) and their activation leads to characteristic morphological changes of the cell such as shrinkage, chromatin condensation, DNA fragmentation and plasma membrane blebbing. Induction to commit suicide is required for proper organismal development, to remove cells that pose a threat to the organism (e.g. cell infected with virus, cancer cells), and to remove cells that have damaged DNA. Cells undergoing apoptosis are eventually removed by phagocytosis.

Initiator caspases are the first to be activated and include caspase-2, 8, 9 and 10. These cleave and activate the effector caspases (3, 6, 7), which cleave, degrade or activate other cellular proteins. Some caspases (1, 4, 5, 11, 12, 13, 14) have a specialized role in inflammation and their activation leads to the processing of pro-inflammatory cytokines.

Caspase-3, also called CPP32, apopain, or YAMA has been identified as being a key mediator of apoptosis of mammalian cells. Caspase-3 zymogens exist within the cytosol as inactive dimmers. Consistent with the proposal that apoptosis plays a central role in human neurodegenerative disease, caspase-3 activation has recently been observed in stroke, spinal cord trauma, head injury and Alzheimer's disease. Indeed, peptide-based caspase inhibitors prevent neuronal loss in animal models of head injury and stroke, suggesting that these compounds may be the forerunners of non-peptide small molecules that halt the apoptotic process implicated in these neurodegenerative disorders (Freude B. et al., Apoptosis is initiated by myocardial ischemia and executed during reperfusion. J Mol Cell Cardiol. 2000 February; 32(2):197-208.).

The N-methyl-D-aspartate (NMDA) subtype of glutamate receptor is a calcium-permeable ligand-gated ion channel that plays an important role in learning and memory. NMDA receptors are heteromeric pentamers or tetramers of NR1 and NR2 receptor subunits that determine the biophysical and pharmacological properties of the receptor. It has been shown that the NR1 subunit contains three transmembrane domains (TM1, TM3, and TM4) and two extracellular domains (S1 and S2), which form the glutamate (or homocysteine) and glycine binding sites, respectively, and a hydrophobic domain (TM2) that forms the pore of the ion channel (B S Meldrum, "The Role of Glutamate in Epilepsy and Other CNS Disorders," Neurology 44S (1994): 14-23.). The NR2 subunit has four further subunits—NR2A, NR2B, NR2C, and NR2D— that are responsible for Na+- and Ca++-permeability regulation. The yellow extracellular loops in the figure are N-terminus fragments of NMDA receptors that are cleaved by thrombin-activated serine proteases during the neurotoxic cascade underlying stroke.

In clinical study, NMDA biomarkers were found to provide real-time evidence of neurotoxicity, with a decrease in levels of circulating NR2A/2B receptor subunits correlating well with reductions in neurotoxic conditions (E I Gusev et al., "Neuroprotective Effects of Glycine for Therapy of Acute Ischaemic Stroke," Cerebrovascular Diseases 10 (2000): 49-60.). These NR2A/2B peptide fragments in human plasma are of molecular weight 2 and 6 kDa, respectively. Subsequent studies have showed a correlation between NR2A/2B levels and TIA and ischemic stroke determination (S A Dambinova, G A Khounteev, and A A Skorometz, "Multiple Panel of Biomarkers for TIA/Stroke Evaluation," Stroke 33 (2002): 1181-1182.). This marker is the subject of United States Patent Application 20030096331, filed Aug. 2, 2001. However, this patent application does not anticipate any other marker besides homocysteine or polyhomocysteine and glutamate or polyglutamate in combination with this marker for diagnosis of stroke or stroke sub-type.

Ubiquitin (Ub) is a small protein that is composed of 76 amino acids. Ub is a heat-stable protein that folds up into a compact globular structure. It is found throughout the cell (thus, giving rise to its name) and can exist either in free form or as part of a complex with other proteins. In the latter case, Ub is attached (conjugated) to proteins through a covalent bond between the glycine at the C-terminal end of Ub and the side chains of lysine on the proteins. Single Ub molecules can be conjugated to the lysine of these proteins, or more commonly, Ub-chains can be attached. Conjugation is a process that depends on the hydrolysis of ATP. Ub is involved in many cell processes. For example, Ub is conjugated to the protein cyclin during the G1 phase of mitosis and thus plays an important role in regulating the cell cycle. Ub conjugation is also involved in DNA repair, embryogenesis, the regulation of transcription, and apoptosis (programmed cell death). The ubiquitin-proteasome pathway (UPP) is a predominantly non-lysosomal protein degradation pathway responsible for degrading many critical regulatory proteins (e.g., nuclear factor-kappa B). This pathway is widely known for its ubiquitous role in immune and inflammatory responses, control of cell growth and apoptosis. These roles are apparent in the nervous system, but neurons and their neighboring cells also employ the UPP for distinct functions, ranging from development to the co-ordination of cellular responses, injury of the nervous system and brain-specific processes such as aging and memory.

Markers Specifically Related to Hemorrhage

Cellular Fibronectin, or ED1+. is an adhesive glycoprotein, is a fibronectin synthesized in endothelial cells. It contains an extra Type III domain (ED1, or EDA/EIIIA), as a result of alternative mRNA splicing. It circulates in the blood in small quantities. Endothelial cells do not express the ED1 domain under normal circumstances, but the ED1 domain is included in fibronectin molecules in pathological conditions (see for instance Dubin D, Peters J H, Brown L F, Logan B, Kent K C, Berse B, Berven S, Cercek B, Sharifi B G, Pratt R E: Balloon catheterization induced arterial expression of embryonic fibronectins. Arterioscler Thromb Vasc Biol. 15:1958 1967, 1995.) Because ED1-fn is not stored in cellular granules, concentration increases indicate increased synthesis (26). Because c-Fn is largely confined to the vascular endothelium, high plasma lvels of this molecule might be indicative of endothelial damage. Plasma c-Fn levels have been reported to be increased in patients with vascular injury secondary to vasculitiis, sepsis, acute major trauma, diabetes, and patients with ischemic stroke (see for instance Peters et al. Elevated plasma levels of ED1+ 'cellular fibronectin' in patients with vascular injury J Lab Clin Med. 1989. 113:586-597). It has been reported to associate with the hemorrhagic transformation (see for instance Castellanos et al., Plasma Cellular-Fibronectin concentration predicts hemorrhagic transformation after thrombolytic therapy in acute ischemic stroke, Stroke 2004; 35:000-000).

How to Measure Various Markers

One of ordinary skill in the art know several methods and devices for the detection and analysis of the markers of the instant invention. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like. For an example of how this procedure is carried out on a machine, one can use the RAMP Biomedical device, called the Clinical Reader sup.™., which uses the fluoresent tag method, though the skilled artisan will know of many different machines and manual protocols to perform the same assay. Diluted whole blood is applied to the sample well. The red blood cells are retained in the sample pad, and the separated plasma migrates along the strip. Fluorescent dyed latex particles bind to the analyte and are immobilized at the detection zone. Additional particles are immobilized at the internal control zone. The fluorescence of the detection and internal control zones are measured on the RAMP Clinical Reader sup.™., and the ratio between these values is calculated. This ratio is used to determine the analyte concentration by interpolation from a lot-specific standard curve supplied by the manufacturer in each test kit for each assay.

The use of immobilized antibodies specific for the markers is also contemplated by the present invention and is well known by one of ordinary skill in the art. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvagable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constucted using 1, 2, 3, 4, 5, 6, 7, 8, 9, 10, 15, 20, or more or individual markers. The analysis of a single marker or subsets of markers comprising a larger panel of markers could be carried out methods described within the instant invention to optimize clinical sensitivity or specificity in various clinical settings. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, 2.sup.nd edition, Carl Burtis and Edward Ashwood eds., W. B. Saunders and Company, p. 496).

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and capillary devices.

In another embodiment, the present invention provides a kit for the analysis of markers. Such a kit preferably comprises devises and reagents for the analysis of at least one test sample and instructions for performing the assay. Optionally the kits may contain one or more means for using information obtained from immunoassays performed for a marker panel to rule in or out certain diagnoses. Marker antibodies or antigens may be incorporated into immunoassay diagnostic kits depending upon which marker autoantibodies or antigens are being measured. A first container may include a composition comprising an antigen or antibody preparation. Both antibody and antigen preparations should preferably be provided in a suitable titrated form, with antigen concentrations and/or antibody titers given for easy reference in quantitative applications.

The kits may also include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present invention are generally well known in the art.

The reagents may also include ancillary agents such as buffering agents and protein stabilizing agents, e.g., polysaccharides and the like. The diagnostic kit may further include where necessary agents for reducing background interference in a test, agents for increasing signal, software and algorithms for combining and interpolating marker values to produce a prediction of clinical outcome of interest, apparatus for conducting a test, calibration curves and charts, standardization curves and charts, and the like.

In a more particular aspect the invention relates to a rapid multiple marker panel containing antibodies to selected markers that employs latex agglutination. Thus, in one embodiment the invention provides a kit for diagnosing stroke or stroke sub-type comprising: (1) an agglutinating immunosorbent for said selected markers, and (2) a control such as saline or a known concentration of said selected markers.

In another embodiment the invention relates to a kit for detecting various markers indicative of stroke or stroke subtype diagnosis comprising: (1) an immunosorbent for selected markers indicative of stroke or stroke subtype diagnosis, and (2) an indicator reagent comprising secondary antibodies attached to a signal generating compound for each individual marker. The secondary antibodies can be specific for each individual marker or for the primary antibodies in the immunosorbent. In a preferred embodiment the kits further comprise an immunosorbent for glutamate or polyglutamate, and/or an immunosorbent for homocysteine or polyhomocysteine, and secondary antibodies against the glutamate and/or homocysteine, or to the primary antibodies on the immunosorbents against the glutamate or homocysteine. The immunosorbent preferably comprises anti-antibodies for the biomarkers bound to a solid support.

In another aspect the present invention relates to a test-kit that relies upon PCR amplification for measuring selected markers indicative of stroke or stroke subtype diagnosis. Thus, in another embodiment the invention provides a kit comprising: (a) one or more oligonucleotide primers attached to a solid phase, (b) indicator reagent attached to a signal-generating compound capable of generating a detectable signal from oligonucleotides, and (c) a control sample (i.e. template cDNA). The reagents may also include ancillary agents such as buffering agents, polymerase agents, and the like. The diagnostic kit may further include, where necessary, other members of the signal-producing system of which system the detectable group is a member (e.g., enzyme and non-enzyme substrates), agents for reducing background interference in a test, agents for increasing the signal, apparatus for conducting a test, and the like.

In another embodiment of test-kit comprises (a) a solid phase to which biological fluids for receiving total DNA including selected marker cDNA indicative of stroke or stroke subtype diagnosis could be attached, (b) oligonucleotide primers, preferably in a ready-to-use PCR buffer, and (c) a control sample (i.e. template cDNA). Ancillary agents as described above may similarly be included.

In another embodiment the invention provides a diagnostic kit for detecting selected markers indicative of stroke or stroke subtype diagnosis autoantibodies comprising (a) a polypeptide of the selected markers indicative of stroke or stroke subtype diagnosis, fragment thereof, or analog or derivative thereof, (b) an indicator reagent comprising a secondary antibody specific for the autoantibody or the polypeptide attached to a signal-generating compound; and (c) a control sample, such as a known concentration of said selected markers indicative of stroke or stroke subtype diagnosis polyclonal antibodies. The reagents may also include ancillary agents such as buffering agents and protein stabilizing agents, e.g., polysaccharides and the like. The diagnostic kit may further include, where necessary, other members of the signal-producing system of which system the detectable group is a member (e.g., enzyme and non-enzyme substrates), agents for reducing background interference in a test, agents to increase the signal, apparatus for conducting a test, calibration and standardization information or instructions, and the like.

Methodology of Marker Selection, Analysis, and Classification

Non-linear techniques for data analysis and information extraction are important for identifying complex interactions between markers that contribute to overall presentation of the clinical outcome. However, due to the many features involved in association studies such as the one proposed, the construction of these in-silico predictors is a complex process. Often one must consider more markers to test than samples, missing values, poor generalization of results, selection of free parameters in predictor models, confidence in finding a sub-optimal solution and others. Thus, the process for building a predictor is as important as designing the protocol for the association studies. Errors at each step can propagate downstream, affecting the generalizability of the final result.

We now provide a brief overview of our process of model development, describing the five main steps and some techniques that the instant invention may use to build an optimal biomarker panel of response for each clinical outcome. A fuller description is given in U.S. patent application Ser. No. 11/046,592 and related applications. One of ordinary skill in the art will know that it is best to use a 'toolbox' approach to the various steps, trying several different algorithms at each step, and even combining several as in Step Five. Since one does not know a priori the distribution of the true solution space, trying several methods allows a thorough search of the solution space of the observed data in order to find the most optimal solutions (i.e. those best able to generalize to unseen data). One also can give more confidence to predictions if several independent techniques converge to a similar solution.

Method for Defining Panels of Markers

In practice, data may be obtained from a group of subjects. The subjects may be patients who have been tested for the presence or level of certain markers. Such markers and methods of patient extraction are well known to those skilled in the art. A particular set of markers may be relevant to a particular condition or disease. The method is not dependent on the actual markers. The markers discussed in this document are included only for illustration and are not intended to limit the scope of the invention. Examples of such markers and panels of markers are described in the instant invention and the incorporated references.

Well-known to one of ordinary skill in the art is the collection of patient samples. A preferred embodiment of the instant invention is that the samples come from two or more different sets of patients, one a disease group of interest and the other(s) a control group, which may be healthy or diseased in a different indication than the disease group of interest. For instance, one might want to look at the difference in blood-borne markers between patients who have had stroke and those who had stroke mimic to differentiate between the two populations.

The blood samples are assayed, and the resulting set of values are put into a database, along with outcome, also called phenotype, information detailing the illness type, for instance stroke mimic, once this is known. Additional clinical details such as time from onset of symptoms and patient physiological, medical, and demographics, the sum total called patient characteristics, are put into the database. The time from onset is important to know as initial marker values from onset of symptoms can change significantly over time on a timeframe of tens of minutes. Thus, a marker may be significant at one point in the patient history and not at another in predicting diagnosis or prognosis of cardiovascular disease, damage or injury. The database can be simple as a spreadsheet, i.e. a two-dimensional table of values, with rows being patients and columns being filled with patient marker and other characteristic values.

From this database, a computerized algorithm can first perform pre-processing of the data values. This involves normalization of the values across the dataset and/or transformation into a different representation for further processing. The dataset is then analyzed for missing values. Missing values are either replaced using an imputation algorithm, in a preferred embodiment using KNN or MVC algorithms, or the patient attached to the missing value is exised from the database. If greater than 50% of the other patients have the same missing value then value can be ignored.

Once all missing values have been accounted for, the dataset is split up into three parts: a training set comprising 33-80% of the patients and their associated values, a testing set comprising 10-50% of the patients and their associated values, and a validation set comprising 1-50% of the patients and their associated values. These datasets can be further sub-divided or combined according to algorithmic accuracy. A feature selection algorithm is applied to the training dataset. This feature selection algorithm selects the most relevant marker values and/or patient characteristics. Preferred feature selection algorithms include, but are not limited to, Forward or Backward Floating, SVMs, Markov Blankets, Tree Based Methods with node discarding, Genetic Algorithms, Regression-based methods, kernel-based methods, and filter-based methods.

Feature selection is done in a cross-validated fashion, preferably in a naïve or k-fold fashion, as to not induce bias in the results and is tested with the testing dataset. Cross-validation is one of several approaches to estimating how well the features selected from some training data is going to perform on future as-yet-unseen data and is well-known to the skilled artisan. Cross validation is a model evaluation method that is better than residuals. The problem with residual evaluations is that they do not give an indication of how well the learner will do when it is asked to make new predictions for data it has not already seen. One way to overcome this problem is to not use the entire data set when training a learner. Some of the data is removed before training begins. Then when training is done, the data that was removed can be used to test the performance of the learned model on "new" data.

Once the algorithm has returned a list of selected markers, one can optimize these selected markers by applying a classifer to the training dataset to predict clinical outcome. A cost function that the classifier optimizes is specified according to outcome desired, for instance an area under receiver-operator curve maximizing the product of sensitivity and specificity of the selected markers, or positive or negative predictive accuracy. Testing of the classifier is done on the testing dataset in a cross-validated fashion, preferably naïve or k-fold cross-validation. Further detail is given in U.S. patent application Ser. No. 09/611,220, incorporated by reference. Classifiers map input variables, in this case patient marker values, to outcomes of interest, for instance, prediction of stroke subtype. Preferred classifiers include, but are not limited to, neural networks, Decision Trees, genetic algorithms, SVMs, Regression Trees, Cascade Correlation, Group Method Data Handling (GMDH), Multivariate Adaptive Regression Splines (MARS), Multilinear Interpolation, Radial Basis Functions, Robust Regression, Cascade Correlation+Projection Pursuit, linear regression, Non-linear regression, Polynomial Regression, Regression Trees, Multilinear Interpolation, MARS, Bayes classifiers and networks, and Markov Models, and Kernel Methods.

The classification model is then optimized by for instance combining the model with other models in an ensemble fashion. Preferred methods for classifier optimization include, but are not limited to, boosting, bagging, entropy-based, and voting networks. This classifier is now known as the final predictive model. The predictive model is tested on the validation data set, not used in either feature selection or classification, to obtain an estimate of performance in a similar population.

The predictive model can be translated into a decision tree format for subdividing the patient population and making the decision output of the model easy to understand for the clinician. The marker input values might include a time since symptom onset value and/or a threshold value. Using these marker inputs, the predictive model delivers diagnositic or prognostic output value along with associated error. The instant invention anticipates a kit comprised of reagents, devices and instructions for performing the assays, and a computer software program comprised of the predictive model that interprets the assay values when entered into the predictive model run on a computer. The predictive model receives the marker values via the computer that it resides upon.

BRIEF DESCRIPTION OF THE DRAWINGS

In the following, the invention will be explained in further detail with reference to the drawings, in which:

FIG. 1 is a table illustrating clinical parameters among a set of m-EHG patients and a set of non-EHG patients;

FIG. 2 is a table showing baseline plama molecular levels at admission among a set of EHG patients and a set of non-EHG patients;

FIG. 3 is a table showing Adjusted Odds Ratios (95% CI) of the Potential Predictors of EHG;

FIG. 4 is a table illustrating clinical parameters among a set of m-MCA patients and a set of non-m-MCA patients;

FIG. 5 is a table showing baseline plama molecular levels at admission among a set of m-MCA patients and a set of non-m-MCA patients; and FIG. 6 is a table illustrating Clinical, Radiological and Biochemical Predictors of m-MCA Infarction

EXAMPLE I

In a prospective, multicenter study performed to identify predictors of early neurological deterioration, 266 patients with primary hemispheric ICH were admitted within 12 hours from the onset of symptoms. Exclusion criteria were age younger than 18, surgical treatment on admission, coma with expected death within 48 hours, and hemorrhage secondary to brain tumor, trauma, drug abuse, coagulation disorders, anticoagulant therapy, or vascular malformation. For the purpose of this study we also excluded patients without stored frozen blood samples obtained on admission (n=74) and those in whom computed tomography (CT) scan was not available at 48 hours (n=4). From the total series of 266 patients, 183 patients were included in the study. Early ICH growth occurred in 54 patients (29.5%), in 15 (22.3%) of 67 patients with baseline ICH <20 mL, and in 39 (33.6%) of 116 patients with baseline ICH $\geq$20 mL. The frequency of EHG in the total series was similar (26.9%), and there were no statistical differences in epidemiological, clinical, radiological, or analytical data between the general population and the target population.

On arrival to the emergency department, blood pressure and body temperature were recorded and blood samples were taken. Each patient underwent a baseline head CT scan and a Canadian Stroke Scale (CSS) evaluation by an experienced neurologist. Patients were admitted to a neurological ward or an acute stroke unit and were treated by a specialized stroke team and nursing staff following established guidelines (see for example Lainez J M et al. Guý'a de actuacio'nclý'nica en la hemorragia cerebral. Neurology'a. 2002; 17(suppl 3):76-86. [In Spanish].). Antihypertensive treatment with intravenous labetalol or captopril was administered in case of systolic blood pressure >185 mm Hg or diastolic blood pressure >105 mm Hg. Low-dose subcutaneous heparin was used for the prevention of deep vein thrombosis and pulmonary thromboembolism. None of the patients was part of a therapeutic clinical trial. A second CT scan was performed at 48±6 hours. The evaluation of all CT scans was performed at the coordinating center by a single investigator who was blinded to the clinical and biochemical data. Lesion volumes were calculated on the radiographic plate using the formula 0.5× a×b×c (where a is the maximal longitudinal diameter, b is the maximal transverse diameter, and c is the number of 10-mm slices containing hemorrhage). The volume of the ICH plus that of the zone of peripheral hypodensity was determined using the same volumetric method described; the absolute volume of the hypodensity was calculated by subtracting the volume of the ICH from that of the total lesion (ICH plus peripheral hypodensity). According to a previous report, relevant EHG was defined as a volume increase >33% between the 2 CT for those ICHs with a baseline volume <20 mL, and a volume increase >10% for those hemorrhages with a baseline volume ≧20 mL (Leira R, Davalos A, Silva Y, Gil-Peralta A, Tejada J, Garcia M, Castillo J. Predictors and associated factors of early neurological deterioration in intracerebral hemorrhage. *Neurology.* 2004; 63:461-467.). Secondary analyses were performed using the >33% growth definition for all patients in a way to be compared with another prospective study in which this definition was used.2 The ICH topography was classified as lobar when it affected predominantly the cortical or subcortical white matter of the cerebral lobes, or as deep when it was limited to the internal capsule, the basal ganglia, or the thalamus. The presence of intraventricular extension of the hematoma, leukoaraiosis, and mass effect was also recorded. Early neurological deterioration (END) was diagnosed when the CSS score decreased 1 or more points between admission and 48 hours after admission. This difference represents the change with the highest sensitivity, retaining good specificity.17 Patients who died within the first 48 hours were classified in the END group if they had progressed during the observations that followed after inclusion. Functional outcome was evaluated by the modified Rankin scale at 90 days. Patients with a modified Rankin scale score>2 were classified in the poor outcome category.

Laboratory Tests

Blood samples were collected on admission in tubes with potassium edetate, centrifuged at 3000 g for 5 minutes, and immediately frozen and stored at −800. IL-6 and tumor necrosis factor-alpha (TNF-α) were measured with commercially available quantitative sandwich enzyme-linked immunosorbent assay (Quantikine) kits obtained from R&D Systems. MMP-9 was measured with commercially available quantitative sandwich enzyme-linked immunosorbent assay kits obtained from Biotrack Amersham Pharmacia, UK. c-Fn was measured with enzyme-linked immunosorbent assay kits obtained from Boehringer, Germany. Laboratory determinations were performed blinded to clinical and neuroimaging findings.

Proportions between groups were compared using the $\chi^2$ test. Continuous variables are expressed as mean±SD and were compared using the Student t test. Given that MMP-9 and c-Fn concentrations are not normally distributed, their levels were expressed as median (quartiles), and comparisons were made using the Mann-Whitney test or Kruskal-Wallis test as appropriate. The association between c-Fn levels and baseline continuous variables was assessed by calculating the Spearman correlation coefficient.

Statistical Analysis

We used cutoff values, as described by Robert et al, (Robert C, Vermont J, Bosson J L. Formulas for threshold computations. *Comput Biomed Res*. 1991; 24:514-519.) to categorize non-linear variables. Potential predictors of EHG in the bivariate analyses (P<0.05) were tabulated and were then analyzed by logistic regression (probability of entry P<0.05). In a further logistic model, we investigated whether predictors of EHG were also independently associated with END, poor functional outcome, and mortality at 3 months. We tested the linearity of the explanatory variables related to the risk of EHG before performing the logistic models. Variables that showed no linearity were categorized by means of the Robert method.18 Moreover, all possible plausible interactions among variables were tested. Results were expressed as adjusted odds ratio with corresponding 95% confidence intervals.

Results

Potential predictors of EHG in the bivariate analysis are shown in FIG. 1. Age, gender, frequency of risk factors, time from symptoms onset to admission, CSS score, body temperature, and blood pressure were similar in both groups. Patients with EHG had larger volume of peripheral hypodensity, higher leukocyte count and plasma fibrinogen levels at admission, and lower platelet count and intraventricular bleeding than did non-EHG patients.

Plasma concentrations of IL-6, TNF-α, MMP-9, and c-Fn were significantly higher in patients with subsequent EHG (FIG. 2). Similar results were found when EHG was defined according to the >33% growth definition for all patients. Concentrations of these molecules by the percentage of change in the ICH volume at 48 hours are shown in the Figure. A highly significant correlation was found between plasma c-Fn and MMP-9 levels on admission and the percentage of ICH growth (r=0.77 and r=0.64, respectively; both P<0.001). Also, a significant moderate correlation was found between baseline TNF-α and IL-6 levels and the percentage of ICH growth (r=0.26 and r=0.32, respectively; both P<0.001).

Because of lack of linearity, IL-6, TNF-α, MMP-9, and c-Fn were classified in 2 categories. Of all these variables associated with EHG in bivariate analyses, plasma c-Fn levels >6 µg/mL and IL-6 levels >24 pg/m were associated with increased risk of EHG in the final logistic model, whereas intraventricular bleeding was associated with a decreased risk (FIG. 3). No interactions were found. c-Fn >6 µg/mL (OR, 297; 95% Cl, 28 to 3128) was the only predictive factor of EHG according to the >33% growth definition for all patients.

The Instant Invention has demonstrated that high plasma levels of c-Fn and IL-6 at baseline are independent predictors of ICH enlargement. The Instant Invention support the idea that molecular signatures in blood of endothelial damage and inflammatory response may help to predict patients with a high risk of subsequent EHG. This fact is clinically relevant, because this study has confirmed that ICH growth is associated with a 3.7-fold increase in the odds of early neurological deterioration and poor functional outcome, and a 5.2-fold increase in the odds of mortality at 3 months.

Higher number of leukocytes and levels of fibrinogen, IL-6, and TNF-α in the peripheral blood were found in patients with EHG, in whom we also found a greater volume of peripheral edema at baseline. Notably, IL-6 levels >24 pg/mL increased 16-fold the risk of EHG after controlling for other markers of inflammation. Intraventricular bleeding appeared to be a protective factor for ICH growth but presumably was caused by the extravasation of blood into the ventricular system. Both MMP-9 and c-Fn concentrations in blood were significantly higher in patients with EHG, and c-Fn was the most powerful predictor of ICH enlargement. Plasma c-Fn levels >6 µg/mL were associated with 92-fold increase in the risk of EHG, and c-Fn levels showed a high correlation with the percentage of the ICH growth.

EXAMPLE II

Subjects and Methods

Plasma glutamate, glycine, γ-aminobutyric acid (GABA), interleukin-6 (IL-6), IL-10, tumor necrosis factor-α (TNF-α), MMP-9 and c-Fn concentrations were determined in 75 patients <70 years of age experiencing a clinically massive MCA infarction <24 hours from stroke onset. Patients were consecutively included in a prospective register with the aim of evaluating serum markers of early and late clinical course. Of 408 acute ischemic stroke patients included during the 1-year study period, 75 patients experienced large/massive strokes (total anterior cerebral infarction [TACI]), met all eligibility criteria, and so were included retrospectively in the present study. Forty of these patients had fatal brain swelling and were designated as having m-MCA infarction. The remaining 35 patients with complete MCA infarction of comparable clinical severity to those of m-MCA infarction served as the control group. Massive MCA infarction was diagnosed in patients with a clinically identifiable TACI syndrome at admission14 and a cerebral infarction involving at least the anterior and posterior divisions of the MCA territory (with or without the deep MCA territory supplied by the lenticulostriate arteries), which is equivalent to two thirds or more of the MCA, as measured in a follow-up computed tomography (CT) scan.

Malignant MCA infarction was diagnosed following the Schwab et al criteria (Schwab S, Steiner T, Aschoff A, Schwarz S, Steiner H H, Jansen O, Hacke W. Early hemicraniectomy in patients with complete middle cerebral artery infarction. *Stroke*. 1998; 29:1888-1893.): clinical evidence of acute, massive MCA infarction demonstrated on follow-up CT including complete space-occupying MCA infarction with midline shift and compression of the basal cisterns, and further neurological deterioration consisting of a decrease in the level of consciousness to somnolence or stupor compared with the baseline clinical status on admission. The protocol was approved by the ethics committees, and informed consent for inclusion in the stroke registry was given by patients or their relatives. Stroke severity was quantified by an experienced neurologist using the Canadian Stroke Scale (CSS) at admission and 24 hours, 48 hours, and 7 days after inclusion. Following already published criteria aimed at giving the highest sensitivity and specificity, early neurological deterioration (END) was diagnosed when the CSS score dropped $\geq 1$ points during the first 48 hours after admission.15 Patients with potential infectious diseases or hyperthermia within the 15 days before stroke were excluded. Outcome at 3 months was evaluated using the modified Rankin scale and the CSS. CT scan was performed at admission. Early signs of cerebral infarction (ESCIs) on CT, including the presence of focal hypodensity consistent with the clinical picture, obscuration of the lenticular nucleus, obscuration of the cortex, and mass effect with effacement of the cortical sulci (grade I), ventricular asymmetry (grade II), or shifting of the structures of the median line (grade III), were evaluated in the first radiological examination. To measure the infarct volume and evaluate the presence of hemorrhagic transformation or mass effect, a second CT was performed between days 4 and 7 of hospitalization, or earlier in the case of neurological deterioration. The infarct volume was determined by the formula 0.5×a× b×c (where a and b are the largest perpendicular diameters measured on CT and c is the slice thickness). Because the extent of MCA ischemia is not included in the prospective stroke registry, we have made a retrospective assessment using the Alberta Stroke Program Early CT Score (AS-PECTS) method and blinded to molecular and clinical data.16 Blood chemistry test, 12-lead ECG, chest radiography, and arterial supra-aortic trunk examination were also performed in all patients. The suspected etiology of brain infarction was classified as large-artery atherosclerosis, cardioembolism, and cryptogenic stroke, following the Trial of Org 10172 in Acute Stroke Treatment (TOAST) criteria. Patients included in clinical trials or treated with recombinant tPA were excluded.

Laboratory Tests

Blood samples were taken on admission at the emergency department in glass test tubes containing potassium edentate and centrifuged at 3000 g for 5 minutes and stored at −80° C. Plasma IL-6, IL-10, TNF-α, MMP-9, and c-Fn were measured with commercially available quantitative sandwich ELISA kits (Quantikine, R & D Systems, Biotrack, Amersham Pharmacia UK, and Adeza Biomedical, respectively). Glutamate, glycine, and GABA were quantified by high-performance liquid chromatography as described elsewhere (Castillo J, Davalos A, Noya M. Progression of ischemic stroke and excitotoxic amino acids. *Lancet*. 1997; 349:79-83.). These measurements were made by technicians blinded to the clinical outcome and neuroimaging findings at an independent laboratory.

Statistical Analyses

Proportions between groups were compared by the $\chi^2$ test. Continuous variables have been expressed as the mean and SD, or median and quartiles in the case of distribution that was not normal, and compared by the Student's t test or the Mann-Whitney test as appropriate. We used cut-off values, as described by Robert et al,19 to estimate the sensitivity, specificity, predictive values, and accuracy (with 95% CI) of a specific concentration of MMP-9 and of c-Fn for m-MCA. This method is a probabilistic technique based on Bayes' rules, which provides the maximum probability of a correct classification. The importance of c-Fn for the development of m-MCA infarction was assessed by logistic regression analysis adjusting for those baseline variables related to m-MCA infarction in the bivariate analysis. However, the model could not estimate the adjusted effect of c-Fn because of the high collinearity among age, MMP-9, and c-Fn. Because the c-Fn is one of the main components of the endothelial basal lamina and the target of MMP-9, and considering its high positive predictive value (PPV), we decided to focus the results and the discussion on the role of c-Fn in predicting m-MCA without taking into account the multivariate analyses.

Results

Forty of the 75 patients included in the study met the criteria of m-MCA infarction. The 35 patients consecutively admitted for a TACI who did not develop m-MCA were used as a control group. FIG. 4 shows the main characteristics of patients with and without m-MCA infarction. Patients with m-MCA infarction were younger than non-m-MCA infarction patients. There were no significant differences in clinical characteristics nor in vital signs or biochemical parameters at admission. Poor outcome was significantly more frequent in patients experiencing m-MCA syndrome. Twenty-seven of 40 patients (67.5%) with m-MCA died, and only 1 (2.5%) of the survivors was independent (modified Rankin $\leq 2$) at 3 months. These same figures were 20% and 22.9% in the non-m-MCA group (all P$\leq$0.01; FIG. 4). ESCIs on CT scan at admission were detected more frequently in patients who later developed m-MCA infarction, although without statistically significant differences compared with the non-MCA group (92.5% versus 74.3%; P=0.06).

FIG. 5 shows the levels of molecular markers at admission. Plasma levels of glutamate were significantly higher in patients who went on to develop m-MCA infarction, whereas inflammatory molecules were not significantly different between the 2 groups. When focusing on markers of basal membrane disruption, baseline MMP-9 and c-Fn concentrations were significantly higher in patients with m-MCA infarction than in controls. We calculated the c-Fn and MMP-9 cut-off values with the highest sensitivity, specificity PPV, and negative predictive value (NPV) for m-MCA infarction development. This analysis showed that plasma MMP-9 concentrations ≧140 ng/mL predicted the development of m-MCA with a sensitivity of 64%, specificity of 88%, PPV of 85%, and NPV of 69%. The sensitivity, specificity, PPV, and NPV of plasma c-Fn ≧16.6 µg/mL for the prediction of m-MCA infarction were 90%, 100%, 100%, and 90%, respectively. FIG. 6 includes the sensitivity, specificity, PPV, and NPV of clinical, radiological and molecular markers of m-MCA infarction.

This example shows that a plasma c-Fn concentration ≧16.6 pg/mL at admission predicts the development of m-MCA infarction with a sensitivity of 90% and specificity of 100%, and therefore is of use in therapeutic decision making.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of determining presence or risk of cerebral injury in a human subject, the method comprising:
   obtaining a test sample from a human subject;
   analyzing the obtained test sample for presence or amount or both presence and amount of (1) cellular fibronectin and (2) one or more additional markers both proteomic and non-proteomic for, or mass spectrometry peak levels from, any of categories of apoptosis, cellular adhesion, cellular injury, coagulation, glial activation, inflammatory mediation, myelin breakdown, thrombosis, and vascular damage; and then
   correlating (1) the presence or amount of said cellular fibronectin and said one or more additional markers or peak levels, with (2) clinical patient information, other than the cellular fibronectin and said one or more makers or peak levels for cerebral injury, in order to deduce a probability of present or future risk or present and future risk of a cerebral injury for the subject; and then
   providing the deduced probability to a clinician who treats the cerebral injury in the human subject in accordance with the deduced probability.

2. The method according to claim 1 wherein the correlating is in order to deduce a probability of present or future risk of cerebral injury of a type drawn from the group consisting of secondary brain edema and early growth of intracerebral hemorrhage (ICH).

3. The method according to claim 2 further comprising:
   determining from the deduced probability whether the subject could benefit from aggressive therapies including decompressive hemicraniectomy and hypothermia.

4. The method according to claim 1 wherein the correlating comprises:
   determining the expression levels or mass spectrometry peak levels of one or more proteomic marker(s) or mass-to-charge ratio(s) and the numerical quantity of one or more non-proteomic marker(s) or mass-to-charge ratio(s) from humans suspected or known to have some form of cerebral injury;
   comparing said determined levels and numerical values to humans known to have said matched type of cerebral injury; and
   training an algorithm to identify patterns of differences in said humans which correlate with the prescience or absence of said matched type of cerebral injury, respectively.

5. The method according to claim 4 wherein the training of the algorithm on characteristic protein levels or patterns of differences includes the steps of
   obtaining numerous examples of (i) proteomic and non-proteomic data, and (ii) historical clinical results corresponding to this proteomic and non-proteomic data;
   constructing an algorithm suitable to map (i) protein expression levels or mass spectrometry peak mass-to-charge ratio(s) and said non-proteomic values as inputs to the algorithm, to (ii) the historical clinical results as outputs of the algorithm;
   exercising the constructed algorithm to so map (i) the said protein expression levels or mass spectrometry peak mass-to-charge ratio(s) and said non-proteomic values as inputs to (ii) the historical clinical results as outputs; and
   conducting an automated procedure to vary the mapping function, inputs to outputs, of the constructed and exercised algorithm in order that, by minimizing an error measure of the mapping function, a more optimal algorithm mapping architecture is realized;

wherein realization of the more optimal algorithm mapping architecture, also known as feature selection, means that any irrelevant inputs are effectively excised, meaning that the more optimally mapping algorithm will substantially ignore said protein expression levels or mass spectrometry peak mass-to-charge ratio(s) and said non-proteomic values that are irrelevant to output clinical results; and wherein realization of the more optimal algorithm mapping architecture, also known as feature selection, also means that any relevant inputs are effectively identified, making that the more optimally mapping algorithm will serve to identify, and use, those input protein expression levels or mass spectrometry peak mass-to-charge ratio(s) and said non-proteomic values that are relevant, in combination, to output clinical results that would result in a clinical detection of disease, disease diagnosis, disease prognosis, or treatment outcome or a combination of any two, three or four of these actions.

6. The method according to claim 5 wherein the constructed algorithm is drawn from the group consisting essentially of: linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; a plurality of algorithms arranged in a committee network; and forward floating search or backward floating search algorithms.

7. The method according to claim 5 wherein the feature selection process employs an algorithm drawn from the group consisting essentially of: linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; recursive feature elimination or entropy-based recursive feature elimination algorithms; a plurality of algorithms arranged in a committee network; and forward floating search or backward floating search algorithms.

8. The method according to claim 5 wherein a tree algorithm is trained to reproduce the performance of another machine-learning classifier or regressor by enumerating the input space of said classifier or regressor to form a plurality of training examples sufficient (1) to span the input space of said classifier or regressor and (2) train the tree to emulate the performance of said classifier or regressor.

9. The method according to claim 2
wherein the correlating so as to deduce the risk of cerebral injury is particularly so as to deduce a risk of early hematoma growth following intercerebral hemorrhage; and wherein the method further comprises:
diagnosing a risk of early hematoma growth following intercerebral hemorrhage by measuring the level of cellular fibronectin (c-Fn) alone;
evaluating the patient's risk of hemorrhage following thrombolytic therapy from said measured level of c-Fn; and
administering stroke therapy as appropriate to the evaluated risk of cerebral injury.

10. The method according to claim 9 wherein the one or more additional markers includes, in addition to cellular fibronectin (c-Fn), the proteomic markers MMP-9, IL-6, TNF-α, TAFI, and PAl-1.

11. The method according to claim 9 wherein the one or more additional markers includes, in addition to cellular fibronectin (c-Fn), a proteomic marker of endothelial injury.

12. The method of claim 1 wherein the analyzing of one or more additional markers in addition to cellular-fibronectin is of one or more markers selected from the group consisting of two or more of the following: Glial fibrillary acidic protein, apolipoprotein Cl (ApoC-I), apolipoprotein CIII (ApoC-III), serum amyloid A (SAA), Platelet factor 4 (PF4), platelet-derived growth factor, antithrombin-III fragment (AT-III fragment), bradykinin, renin, haptoglobin, Creatine kinase brain band (CK-BB), adenylate kinase, lactate dehydrogenase, troponin I, troponin T, Brain Derived Neurotrophic Factor, CPK, LDH Isoenzymes, Thrombin-Antithrombin III, calcitonin, procalcitonin, c-tau, Protein C, Protein S, fibrinogen, Factor VIII, activated Protein C resistance, E-selectin, P-selectin, von Willebrand factor (vWF), platelet-derived microvesicles (PDM), plasminogen activator inhibitor-1 (PAI-1), angiotensin I, angiotensin II, angiotensin III, annexin V, arginine vasopressin, B-type natriuretic peptide (BNP), pro-BNP, atrial natriuretic peptide (ANP), N-terminal pro-ANP, pro- ANP, C-type natriuretic peptide, (CNP), c-fos, c-jun, ubiquitin, cytochrome C, beta-enolase, cardiac troponin I, cardiac troponin T, urotensin II, creatine kinase-MB, glycogen phosphorylase-BB, KL-6, endothelin-1, endothelin-2, and endothelin-3, A-, F-, and H-Fatty acid binding protein (A-, F-, H-FABP), phosphoglyceric acid mutase-MB, aldosterone, S-100beta (S100), myelin basic protein, NR2A or NR2B NMDA receptor or fragment thereof (a subtype of N-methyl-D-aspartate (NMDA) receptors), Intracellular adhesion molecule (ICAM or CD54), Neuronal cell adhesion molecule, (NCAM or CD56), C-reactive protein, caspase-3, cathepsin D, hemoglobin alpha.sub.2, human lipocalin-type prostaglandin D synthase, interleukin-1 beta, interleukin-1 receptor angonist, interleukin 2, interleukin 2 receptor, interleukin-6, IL-1, IL-8, IL-10, monocyte chemotactic protein-1, soluble intercellular adhesion molecule-1, soluble vascular cell adhesion molecule-1, MMP-2, MMP-3, MMP-9, MMP-12, MMP-9, tissue factor (TF), NDKA, RAGE, RNA-BP, TRAIL, TWEAK, UFD1, fibrin D-dimer (D-dimer), total sialic acid (TSA), TpP, heat shock protein 60, heat shock protein 70, tumor necrosis factor alpha, tumor necrosis factor receptors 1 and 2, VEGF, Calbindin-D, Proteolipid protein RU Malendialdehyde, neuron-specific enolase gamma gamma isoform (NSE γγ isoform), thrombus precursor protein, Chimerin,-Fibrinopeptide A (FPA), plasmin-α 2AP complex (PAP), plasmin inhibitory complex (PIC), beta-thromboglobulin (β TG), Prothrombin fragment 1+2, PGI2, Creatinine phosphokinase brain band, neurotrophin-3(NT-3), neurotrophin-⅘ (NT-⅘), neurokinin A, neurokinin B, neurotensin, neuropeptide Y, Lactate dehydrogenase (LDH), soluble thrombomodulin (sTM), Insulin-like growth factor-1 (IGF-1), protein kinase C gamma (PKC-γ, Secretagogin, PGE2, 8-epi PGF.sub.2alpha and Transforming growth factor βeta (TGF-β) or markers related thereto.

13. The method of claim 11
wherein the correlating is further so as to determine diagnostic or prognostic outcome; and
wherein the correlating is performed in accordance with an algorithm drawn from the group consisting essentially of: linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; recursive feature elimination or entropy-based recursive feature elimination algorithms; a plurality of algorithms arranged in a committee network; and forward floating search or backward floating search algorithms.

14. The method of claim 13 wherein the correlating so as to further determine diagnostic outcome is, in addition to risk of cerebral injury, expanded to predict risk of malignant massive cerebral artery infarction.

15. The method of claim 1 wherein correlating is of clinical patient information selected from a group consisting of Complete blood count (CBC), Coagulation test, Blood chemistry (glucose, serum electrolytes {Na, Ca, K}), Leukocyte and Neutrophil counts, platelet count, and Blood lipids tests.

16. The method of claim 1 wherein the correlating is of clinical patient information is selected from a group consisting of age, weight, body mass index, computed tomography scan information, Magnet Resonance Image scan information, gender, time from onset of stroke-like symptoms, time to recanalization, ethnicity, heart rate, blood pressure, respiration rate, blood oxygenation, previous personal and/or familial history of cardiac events, recent cranial trauma and unequal eye dilation.

17. The method of claim 1
wherein the analyzing is of both proteomic and non-proteomic markers; and
wherein the correlating is further so as to deduce diagnostic or prognostic outcome.

18. The method of claim 1
wherein the obtaining of the test sample from the subject is within a specific time window from onset of symptoms; and
wherein the correlating is between (1) proteomic and non-marker marker values, and (2) the probability of present or future risk of a cerebral injury for the subject, for said specific time window from onset of symptoms.

19. The method of claim 1
wherein the correlating is in accordance with an algorithm drawn from the group consisting essentially of: linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; recursive feature elimination or entropy-based recursive feature elimination algorithms; a plurality of algorithms arranged in a committee network; and forward floating search or backward floating search algorithms.

* * * * *